(12) United States Patent
Takeyama

(10) Patent No.: US 10,417,446 B2
(45) Date of Patent: Sep. 17, 2019

(54) INFORMATION MANAGEMENT APPARATUS AND METHOD FOR MEDICAL CARE DATA, AND NON-TRANSITORY COMPUTER READABLE MEDIUM

(71) Applicant: FUJIFILM Corporation, Tokyo (JP)

(72) Inventor: Shinichi Takeyama, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 779 days.

(21) Appl. No.: 15/064,614

(22) Filed: Mar. 9, 2016

(65) Prior Publication Data

US 2016/0267227 A1    Sep. 15, 2016

(30) Foreign Application Priority Data

Mar. 10, 2015 (JP) .................... 2015-046949

(51) Int. Cl.
| | |
|---|---|
| H04L 29/06 | (2006.01) |
| H04L 29/08 | (2006.01) |
| G06F 21/62 | (2013.01) |
| G16H 10/60 | (2018.01) |
| G06F 19/00 | (2018.01) |

(52) U.S. Cl.
CPC .......... *G06F 21/6245* (2013.01); *G06F 19/00* (2013.01); *G16H 10/60* (2018.01)

(58) Field of Classification Search
CPC ........ G16H 10/60; G16H 40/20; G16H 50/70; G16H 50/30; G16H 50/20; G16H 50/80; G06F 19/00; G06F 21/6263; G06F 19/325; G06F 19/3456; G06F 19/326; G06F 21/6245; G06Q 50/24

See application file for complete search history.

(56) References Cited

U.S. PATENT DOCUMENTS

| | | | | |
|---|---|---|---|---|
| 2013/0185096 A1* | 7/2013 | Giusti | ..................... | G06Q 50/24 705/3 |
| 2015/0058627 A1* | 2/2015 | Paffel | ..................... | G16H 10/60 713/168 |
| 2016/0006715 A1* | 1/2016 | Lee | ........................ | H04L 63/083 713/155 |

FOREIGN PATENT DOCUMENTS

JP    2014-174635    9/2014

* cited by examiner

*Primary Examiner* — Maroun P Kanaan
(74) *Attorney, Agent, or Firm* — JCIPRNET

(57) ABSTRACT

An information sharing apparatus (management apparatus) for medical care data of a patient body includes a data uploader for classifying the medical care data into confidential data for a primary use in medical care of the patient body, and published data published for a secondary use different from the primary use, to store the confidential data and the published data in a storage medium. A problem event detector monitors the confidential data being added or updated, to check occurrence of a problem event of clinical exacerbation of the patient body. An activation processor checks occurrence of a flag signal for activating relocation of the confidential data to the published data upon the occurrence of the problem event. A relocation unit filters the confidential data at least partially to produce published data upon occurrence of the flag signal after the occurrence of the problem event.

12 Claims, 18 Drawing Sheets

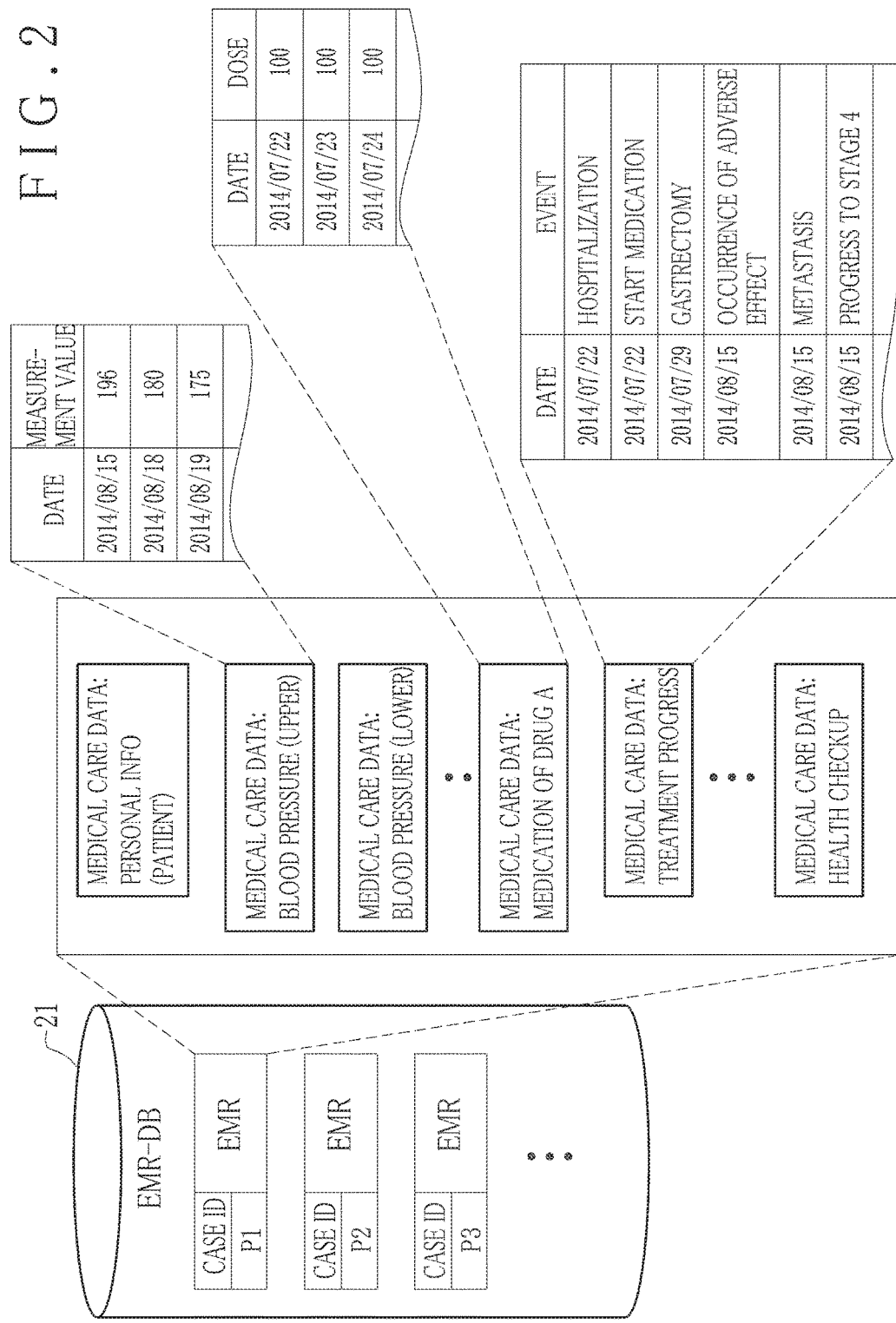

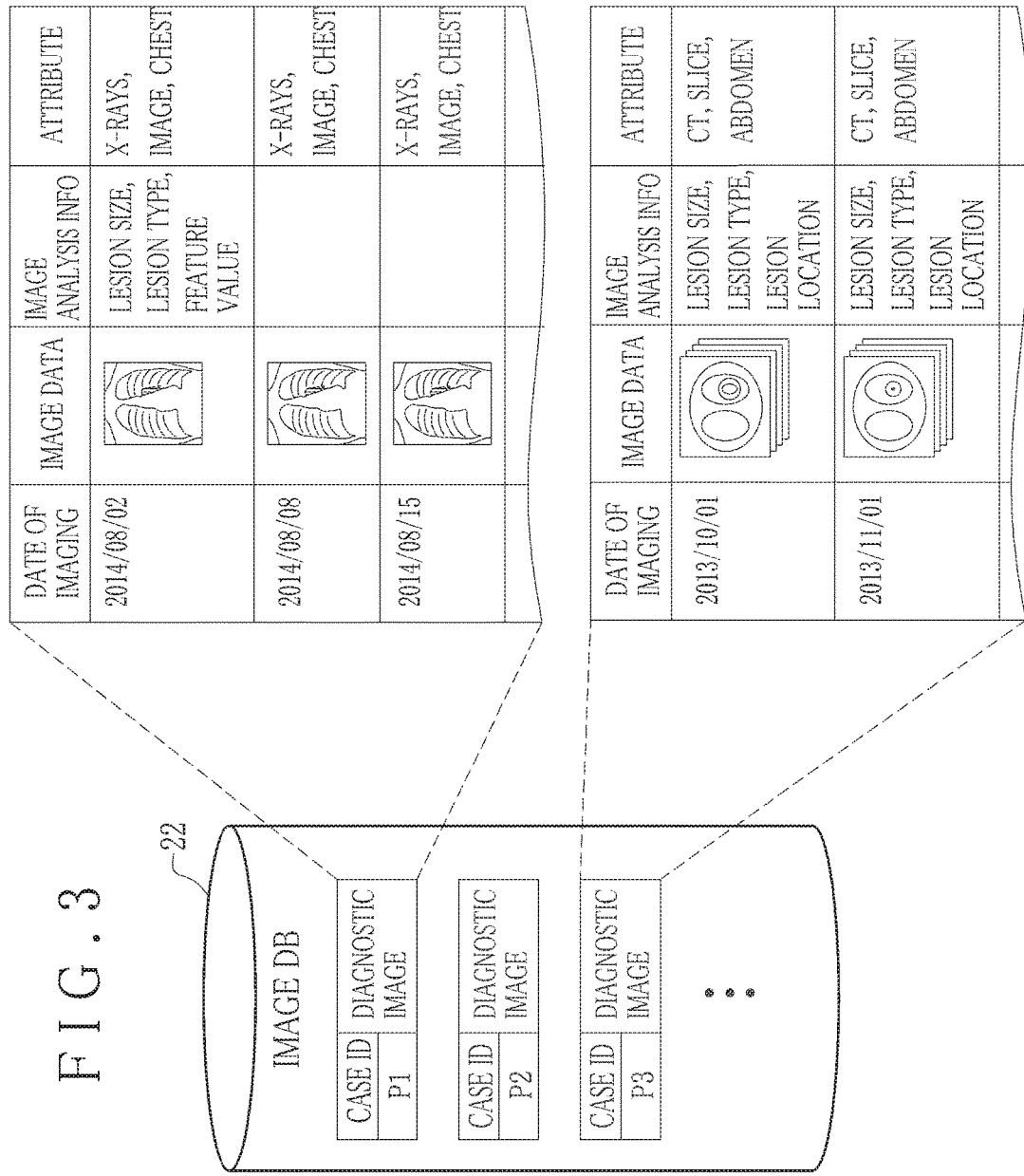

FIG. 4A

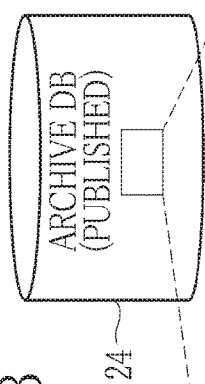

SERVER DB (CONFIDENTIAL) 23

| CASE ID | PERSONAL INFO | | |
|---|---|---|---|
| P1 | Ken Fuji, 1/1/1970, Age 45, M, Blood Type B | | |
| PATIENT VISIT DATA | | | |
| TREATMENT PROGRESS | | | |
| GENETIC INFO | | | |
| CASE ID | PERSONAL INFO | | |
| P2 | Hanako Sato, 2/3/1975, Age 40, F, Blood Type A | | |
| PATIENT VISIT DATA | | | |
| TREATMENT PROGRESS | | | |
| GENETIC INFO | | | |

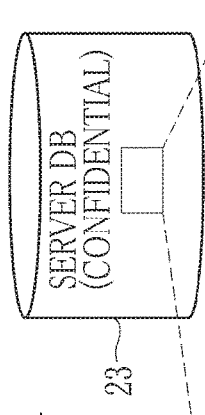

ARCHIVE DB (PUBLISHED) 24

| PATIENT 1: AGE 40S, M |
|---|
| HEALTH CHECKUP |
| COMPLETE MEDICAL CHECKUP |
| PATIENT 2: AGE 40S, F |
| HEALTH CHECKUP |
| COMPLETE MEDICAL CHECKUP |

...

| STATISTICAL DATA (LUNG CANCER) |
|---|
| STATISTICAL DATA (LUNG CANCER & DRUG A) |
| STATISTICAL DATA (DIABETES) |

F I G . 5
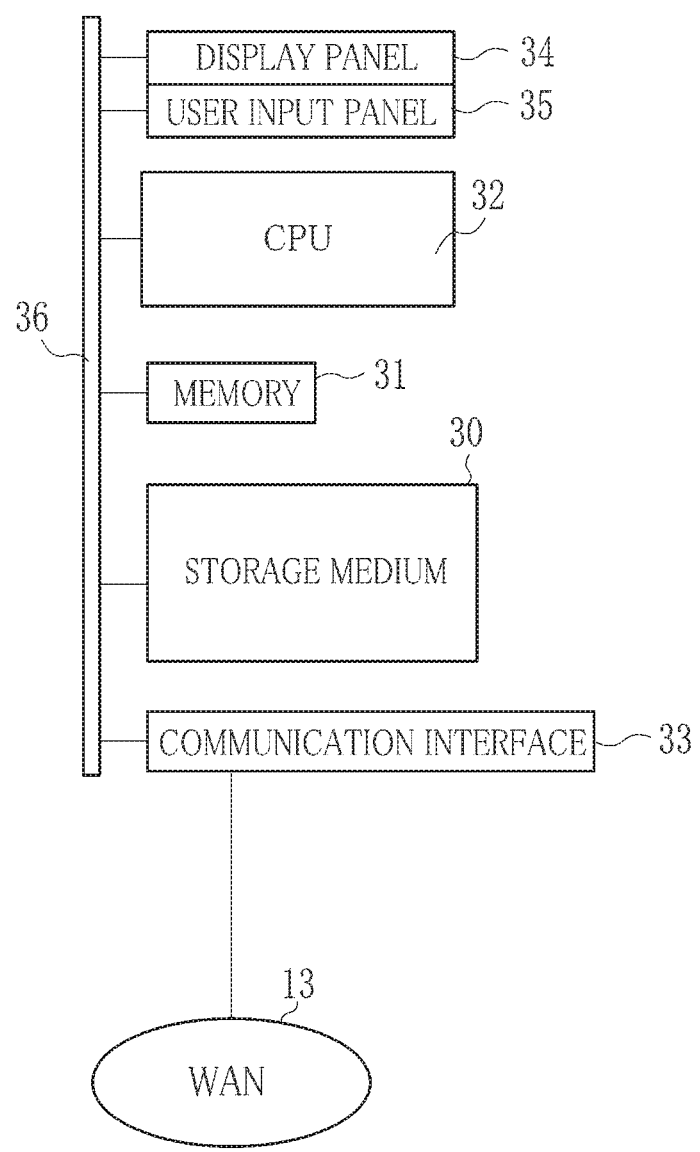

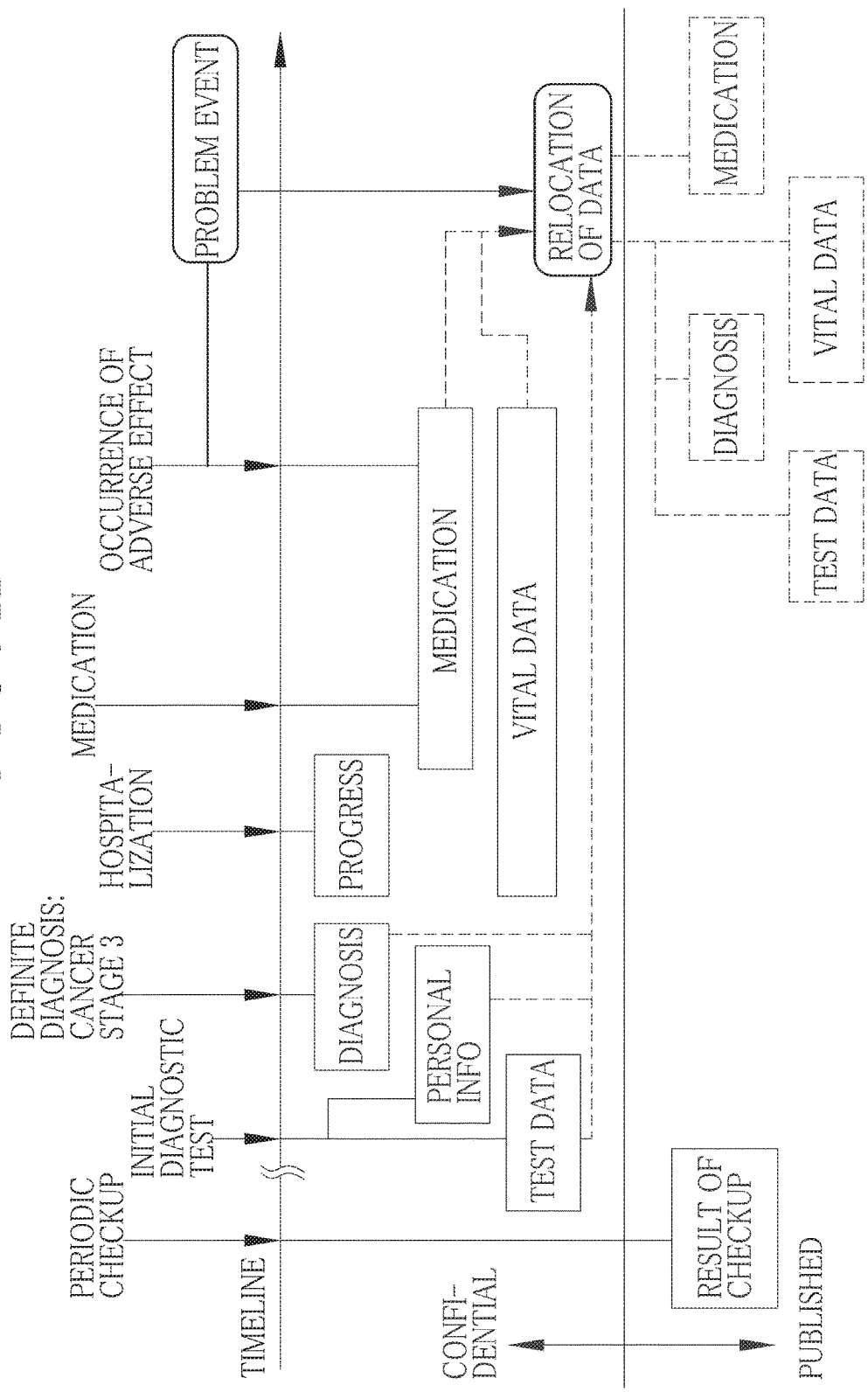
F I G. 12

F I G . 14
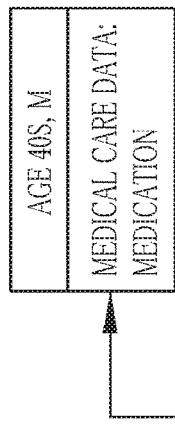
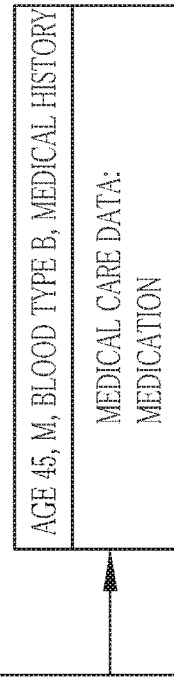
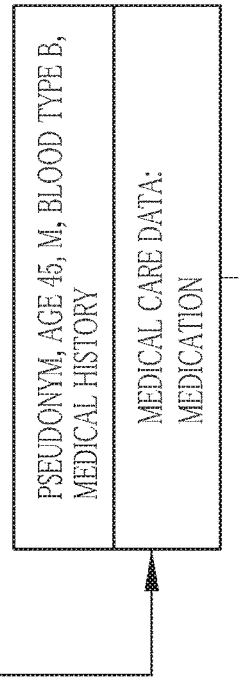
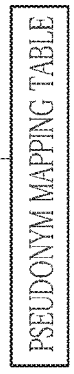

INFORMATION MANAGEMENT APPARATUS AND METHOD FOR MEDICAL CARE DATA, AND NON-TRANSITORY COMPUTER READABLE MEDIUM

CROSS-REFERENCE TO RELATED APPLICATION

This application claims priority under 35 USC 119 from Japanese Patent Application No. 2015-046949, filed 10 Mar. 2015, the disclosure of which is incorporated by reference herein.

BACKGROUND OF THE INVENTION

1. Field of the Invention

The present invention relates to an information management apparatus and method for medical care data, and non-transitory computer readable medium. More particularly, the present invention relates to an information management apparatus and method for medical care data, in which medical care data of patients can be utilized for a secondary use in addition to a primary use in an enhanced form with reliability and safety, and non-transitory computer readable medium.

2. Description Related to the Prior Art

JP-A 2014-174635 discloses a system for enabling a particular user to read and utilize medical care data stored in a particular one of hospital facilities. According to the document, the patient can read his or her medical care data in the medical history. Also, a certain doctor in a first one of the hospital facilities of a patient can view the medical care data of a second one of the hospital facilities where the patient have been diagnosed or treated in his or her medical history. In the disclosure, it is possible to set a status of permission of view for each one of list items of the data. The medical care data of the past can be currently utilized for medical care of the patient, because remote access can be performed by the first hospital facility to the medical care data of the past in the second hospital facility.

In JP-A 2014-174635, the medical care data of patients are used mainly for a primary use of medical care of the patients themselves. However, the medical care data may be utilized for a secondary use other than the primary use, for example, for reference in treatment of other patients in a form of similar patient cases, and for sample information in basic medical research. Processing of big data of a large data amount has been developed recently in the course of development of the information technology. The secondary use of the medical care data of a great number of patients are of a recent concern in the medical field in a form of big data.

However, the medical care data is information relevant to the privacy. The use of the medical care data in a form of identifiable individual patients is inhibited in the secondary use except after receiving patient consent from the patients, as their privacy must be strictly protected. The value of the medical care data is high with clarified attribute data of the respective patients in view of the secondary use, such as an age, sex, blood type, medical history, genetic information and the like. However, a very rare example of the attribute data may lead possibility of identifying a patient only with the attribute data even after deletion of the patient name, for example, a very rare blood type. There is a problem in that the medical care data does not have benefits for the secondary use assuming that all of the attribute data are deleted from the medical care data by considering an identifiable form of the patient.

According to social survey, numerous patients are highly aware of protecting their privacy, and also have personal wish for beneficial contribution in utilizing the medical care data for a secondary use of research and the like in view of purpose of development and innovation of the medicine to support numerous patients in the world. Elderly patients, and also patients with severity after exacerbation of their symptoms are likely to have much concern about the beneficial contribution. In short, the use of the medical care data can be conditioned with certain priority to the beneficial contribution over the ensured protection of the privacy of the patients.

Assuming that there is a technique for supporting the secondary use of the medical care data for the beneficial contribution of data of the patient, collection of the medical care data may be enhanced in addition to statistical data, to enlarge innovation of the secondary use of the medical care data. However, JP-A 2014-174635 only discloses the primary use of the medical care data of the past. There is no suggestion of structures for new development and solution in the use of the medical care data.

SUMMARY OF THE INVENTION

In view of the foregoing problems, an object of the present invention is to provide an information management apparatus and method for medical care data, in which medical care data of patients can be utilized for a secondary use in addition to a primary use in an enhanced form with reliability and safety, and non-transitory computer readable medium.

In order to achieve the above and other objects and advantages of this invention, an information management apparatus for medical care data of a patient body includes a data uploader for classifying the medical care data into confidential data for a primary use in medical care of the patient body, and published data published for a secondary use different from the primary use, to store the confidential data and the published data in a storage medium. A problem event detector monitors the confidential data being added or updated, to check occurrence of a problem event of clinical exacerbation of the patient body. A relocation unit operates assuming that the problem event has occurred, for performing preparatory processing in order to relocate the confidential data at least partially to the published data.

Preferably, furthermore, a data output unit outputs the published data stored in the storage medium.

Preferably, the preparatory processing is transmission of request message information to the patient body for requesting patient consent to publishing the confidential data at least partially.

Preferably, the relocation unit performs relocation of the confidential data at least partially to the published data upon receiving the patient consent from the patient body after the request message information.

Preferably, assuming that the patient consent is not received even upon lapse of a predetermined time after transmitting the request message information, it is judged in the preparatory processing that presumed patient consent is received, so that the relocation is performed.

Preferably, the problem event is constituted by at least one of occurrence of adverse effect of a drug, occurrence of exacerbation in a diagnostic test value, and medical diagnosis of detecting progress of a disease period of the patient body.

Preferably, the problem event is occurrence of adverse effect with the drug. Furthermore, a data searcher searches and detects a typically grouped patient body to whom the drug has been administered commonly among patient bodies different from patient bodies of detection of the occurrence of the adverse effect. A statistical processor produces statistical data from the confidential data of the typically grouped patient body after detection, the statistical data being in a form with which the patient body is unidentifiable. The relocation unit starts the preparatory processing of the confidential data of the patient bodies of the detection of the occurrence of the adverse effect, and relocates the statistic data to the published data.

Preferably, furthermore, a status updater sets a content item included in the confidential data for relocation to the published data for each type of the problem event.

Preferably, the content item is settable respectively for the patient body.

Preferably, the problem event detector further checks occurrence of a specific event predetermined clinically in the medical care of the patient body. The relocation unit performs the preparatory processing in case it is judged that the specific event has occurred.

Preferably, furthermore, an anonymizer anonymizes the confidential data to be relocated to the published data.

Preferably, the anonymizer performs anonymization of which a level is changeable according to at least one of a type of the problem event and a type of the confidential data to be relocated.

Preferably, the storage medium includes a first storage area for storing the confidential data, and a second storage area, separate from the first storage area physically, for storing the published data.

Preferably, the relocation unit includes a filtering device for filtering the confidential data after the preparatory processing, to produce the published data by excluding a data portion in the confidential data different from a data portion therein corresponding to a content item to be relocated.

Also, an information management method for medical care data of a patient body includes a step of classifying the medical care data into confidential data for a primary use in medical care of the patient body, and published data published for a secondary use different from the primary use, to store the confidential data and the published data in a storage medium. The confidential data being added or updated is monitored, to check occurrence of a problem event of clinical exacerbation of the patient body. Assuming that the problem event has occurred, preparatory processing is performed in order to relocate the confidential data at least partially to the published data.

Also, a non-transitory computer readable medium for storing a computer-executable program enabling execution of computer instructions to perform operations for information management for medical care data of a patient body is provided. The operations include classifying the medical care data into confidential data for a primary use in medical care of the patient body, and published data published for a secondary use different from the primary use, to store the confidential data and the published data in a storage medium. The operations include monitoring the confidential data being added or updated, to check occurrence of a problem event of clinical exacerbation of the patient body. Assuming that the problem event has occurred, preparatory processing is performed in order to relocate the confidential data at least partially to the published data.

Consequently, medical care data of patients can be utilized for a secondary use in addition to a primary use in an enhanced form with reliability and safety, because preparatory processing is performed in order to relocate confidential data of medical care to published data.

BRIEF DESCRIPTION OF THE DRAWINGS

The above objects and advantages of the present invention will become more apparent from the following detailed description when read in connection with the accompanying drawings, in which:

FIG. 2 is a data chart illustrating EMRs (electronic medical records);

FIG. 3 is a data chart illustrating diagnostic images;

FIG. 4A is a data chart illustrating a server database for confidential data;

FIG. 4B is a data chart illustrating an archive database for published data;

FIG. 5 is a block diagram schematically illustrating a computer constituting a management server apparatus (information management apparatus);

FIG. 12 is a timing chart illustrating relocation of a data in relation to another patient;

FIG. 14 is a data chart illustrating a third preferred embodiment;

DETAILED DESCRIPTION OF THE PREFERRED EMBODIMENT(S) OF THE PRESENT INVENTION

[First Embodiment]

Figure 1:
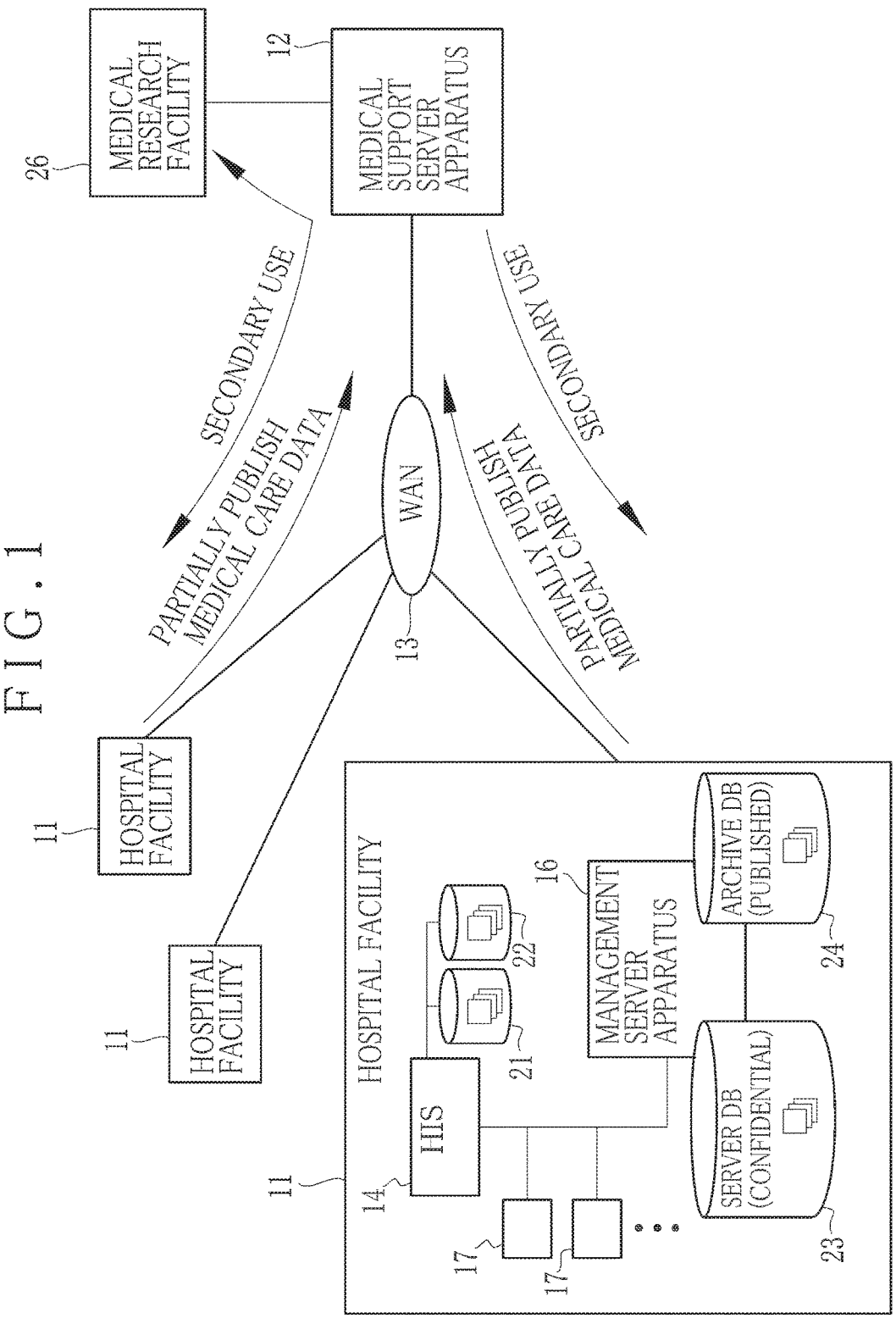
FIG. 1 is a block diagram schematically illustrating a medical network system architecture.

In FIG. 1, a medical network system or medical network system architecture is constituted by medical data systems (medical data system frameworks) of plural hospital facilities 11 or medical service providers, and a medical support server apparatus 12 disposed externally to the hospital facilities 11. A WAN 13 or wide area network interconnects the medical data systems and the medical support server apparatus 12 in a communicable manner. The WAN 13 uses a wide IP network (Internet Protocol Network) managed by a communication service provider as a base network. The WAN 13 is a closed network by establishing VPN (Virtual Private Network) on the basis of the wide IP network. The use of the VPN prevents leakage of information and ensures the security.

The medical data system (medical data system framework) includes a HIS 14 or hospital information system, a management server apparatus 16 or information management apparatus (information sharing apparatus), and a client terminal apparatus 17.

The HIS 14 as a well-known system is a basis of an information system in the hospital facilities 11, and includes various subsystems, such as an EMR system, medical payment system, request system for checkup and diagnostic test. An EMR database 21 or DB for EMRs (electronic medical records) and an image database 22 or DB are combined with the HIS 14. EMRs containing medical care data are stored in the EMR database 21 for the respective patients, such as patient visit data (consultation data) and treatment progress data. Diagnostic images are stored in the image database 22 for the respective patients as medical care data. In the course of medical care of the patient, addition and updating are performed for medical care data stored in the EMR database 21 and the image database 22.

In the present embodiment, the image database 22 is managed by the HIS 14. However, a medical system such as PACS (Picture Archiving and Communication System) can be introduced discretely from the HIS 14 to manage the image database 22.

The client terminal apparatus 17 is a local terminal apparatus for use by a medical professional in a hospital department in the hospital facilities 11, for example, department of the internal medicine, surgical department, and the like. The client terminal apparatus 17 is connected to the EMR database 21 and the image database 22 communicably by a LAN or Local Area Network, and used for inputting or viewing the medical care data.

The management server apparatus 16 is connected to the EMR database 21 and the image database 22 by use of the LAN in an accessible form. The management server apparatus 16 is a server for relocating medical care data to a published form (open archival) for external use after acquisition from the EMR database 21 or the image database 22.

Medical care data are private data of respective patients, and collected from patients for a primary use of medical care of the patients. The medical care data owned by the hospital facilities 11 cannot be used for a purpose other than the primary use. However, the medical care data can be valuable for a secondary use. It is conceivable to utilize the medical care data of patients for the secondary use.

Note that the term of the secondary use is used to express use of medical care data collected for the purpose of the primary use for a purpose other than that of the primary use. Examples of the secondary use (open archival) include use of similar patient cases for reference in medical care of other patients, and use for sample information in basic medical research, medical education for teaching medical students, or other researches. In general, there are patients having personal wish for beneficial contribution in the use of his or her medical care data for the purpose of the secondary use, because this use is important for social contribution of patients in the field of the medicine.

The management server apparatus 16 in the hospital facilities 11 classifies medical care data of patients into confidential data or unpublished data only for the primary use, and published data in publication for the secondary use other than the primary use. The management server apparatus 16 includes a server database 23 or DB as a storage medium (client database) for confidential data or unpublished data, and an archive database 24 or DB as a storage medium for published data. Among the medical care data from the EMR database 21 and the image database 22, medical care data classified as confidential data are registered in the server database 23. Medical care data classified as published data are registered in the archive database 24. The published data registered in the archive database 24 as part of the medical care data are externally published. To this end, the management server apparatus 16 provides the published data to the medical support server apparatus 12.

The medical support server apparatus 12 is a server installed in a location external from the hospital facilities 11, and provides an application service for information distribution of published data from the management server apparatus 16 to the hospital facilities 11, or a medical research facility 26 or medical research laboratory.

The hospital facilities 11 include a particular hospital which provides medical care data to the medical support server apparatus 12, and also which uses medical care data of other hospital facilities for the secondary use. The particular hospital is supplied with medical care data by the other hospital facilities, and uses those for similar case search and the like. Also, the medical research facility 26 is supplied with medical care data by the medical support server apparatus 12 and utilizes those for basic medical research, medical education and the like.

In FIG. 2, EMRs are stored in the EMR database 21 for respective patients. Case IDs are allocated to the EMRs, such as P1, P2, P3 and so on, to manage the EMRs.

Medical care data in the EMRs include the case ID, personal name, and personal information of each of the patients. The personal information includes a residence (address), age (birthday), sex, medical history, genetic information and other attributes. Also, medical care data are recorded in the EMRs, and include patient visit data (consultation data), diagnostic test data, measurement data, request data, and treatment progress data. Examples of the patient visit data include results of questionnaire, finding of progress, symptom name and the like. Examples of the diagnostic test data include test values of diagnostic tests, such as a blood test, biochemical test and other diagnostic tests, and electroencephalography (EEG) and other physiological tests. Examples of the measurement data include measurement values of vital signs, such as respiration rate, heart rate, blood pressure, body temperature and the like. Examples of the request data are for requesting a diagnostic test, treatment, surgery, drug administration and the like. Examples of the treatment progress data include event information of medical processes (events) of a patient body, such as a first patient visit, hospitalization, hospital discharge, rehospitalization, conversion between hospital departments, medical intervention, surgery (such as gastrectomy), drug administration, complete cure and the like.

Information of the medical event includes a procedure of a surgery, for example, gastrectomy, occurrence of adverse effect with a drug, occurrence of metastasis of a cancer, cancer stages of progress of the cancer, for example, change from stage 3 to stage 4, and the like. Also, medical care data related to drug administration are input assuming that the use of the drug is continued for a predetermined period, in addition to the medical care data related to the treatment. The medical care data can include time-sequential information of dose of the drug.

Assuming that there is a healthcare record of a daily health condition of the patient, such as results of a health checkup and complete medical checkup of a periodic manner, and vital data of a body temperature, blood pressure and the like of the patient, then the healthcare record is also input to the EMR database 21 as medical care data. Various medical care data for EMRs can be input by the client terminal apparatus 17, and can be viewed by use of the client terminal apparatus 17.

In FIG. 3, diagnostic images are stored in the image database 22 as medical care data. Case IDs such as P1, P2, P3 and so on are allocated to the diagnostic images, which are managed for the respective patients in the same manner as the EMRs.

The diagnostic images are formed by imaging of various modalities, such as CT imaging (Computed Tomography imaging), MRI imaging (Magnetic Resonance Imaging), non-tomographic X-ray imaging, ultrasound imaging, endoscopic imaging and the like. For example, the diagnostic images are in a format according to the DICOM (Digital Imaging and Communications in Medicine). The diagnostic images can be viewed by use of the client terminal apparatus 17.

Various attributes are associated with the diagnostic image, including a case ID, a calendar date of imaging, image analysis information, modality of the imaging, image type, body part and the like. Examples of the modality include X-ray imaging, CT imaging and the like. Examples of the image type include an X-ray image, slice and the like. Examples of the body part include a chest, abdomen and the like.

In the non-tomographic X-ray imaging, one image is created generally in one diagnostic process of the imaging. In the CT imaging, in contrast, a plurality of the diagnostic images (slices) are created in one diagnostic process of imaging. For this case, a common request ID is allocated to the diagnostic images (slices) to express that the diagnostic images are derived from the single diagnostic process of imaging. The diagnostic images are managed as one group. This is the same assuming that a plurality of X-ray images are created in one diagnostic process of the imaging.

The image analysis information is information related to a location and size of a lesion in the image, a type, feature amount and cure level of the lesion, and the like. Assuming that the imaging is ultrasound imaging, the image analysis information includes a measured value of a blood flow obtained by analyzing the ultrasound image.

The medical care data acquired from the EMR database 21 and the image database 22 are classified into confidential data or unpublished data, and published data. In FIGS. 4A and 4B, the confidential data is registered in the server database 23. The published data is registered in the archive database 24. The server database 23 and the archive database 24 area storage medium according to the present invention.

The server database 23 and the archive database 24 are established by use of different hardware, for example, plural server apparatuses discrete from one another. A storage area of the published data is physically separate from that of the confidential data. Even though the access to the archive database 24 is permitted, improper access to the server database 23 can be prevented with safety, because of the physical separation between the storage areas of the published data and the confidential data. It is possible to ensure information security of the confidential data.

The medical care data acquired from the EMR database 21 and the image database 22 by the management server apparatus 16 are generally classified into confidential data in an initial step of the acquisition, and registered in the server database 23. As described heretofore, the medical care data in the EMR database 21 and the image database 22 are collected for the primary use, and closely related to privacy of the respective patients. Open use of the medical care data for a secondary use without patient consent is unallowable, because the medical care data may be used in the secondary use distinct from the primary use with ensured consent of the patient, in a form of violating the privacy of the patient in the published form of the medical care data.

In the server database 23, all of medical care data collected from the EMR database 21 and the image database 22 are registered for respective patients by use of their case IDs, such as P1, P2, P3 and so on. The server database 23 stores personal information of the patients, and other data with which patients are identifiable. Examples of the confidential data with which patients are specially identifiable include attributes of the patients, such as a name, age, sex, blood type and the like, and also a history of procedures of cosmetic surgery, records of infection of HIV virus (Human Immunodeficiency Virus), records of committing suicide, a history of past diseases, disorders or injury (such as mental disorders), and genetic information. Examples of the genetic information may include information of a carrier of inherited cancer genes, and a history of an onset of atopic dermatitis, autism and the like. Also, the onset history data of such diseases can be classified in the group of patient history data.

Addition or updating is performed for the medical care data in the EMR database 21 and the image database 22 in the course of progress of the medical care of the patient. The management server apparatus 16 performs periodic access to the EMR database 21 and the image database 22, and monitors the addition and updating of the medical care data in the EMR database 21 and the image database 22. Upon occurrence of the addition and updating, addition and updating is also performed for confidential data registered in the server database 23. In short, changes are made for the server database 23 in the same manner as the changes for the EMR database 21 and the image database 22.

The medical care data classified as published data is data after patient consent for the published form. Examples of medical care data as initially classified published data are checkup result data of health checkup and complete medical checkup as illustrated in FIG. 4B. In general, it is relatively easy to acquire the patient consent for the published form in relation to the checkup result data, because the checkup result data is less seriously handled than record of diseases and injuries in the patient visit data and treatment progress data. Consequently, it is preferable to acquire previous patient consent in relation to medical care data of the checkup result data, which can be safely registered as published data.

The published data registered in the archive database 24 in the published form is anonymized to disable identification of individual patients in medical care data. Let patients have case ID of P1 and P2 in FIGS. 4A and 4B. There is no registration of the name, blood type and residence (address) having specifically high relationship to the identification among plural sets of the personal information, such as a name, birthday (age), sex, blood type and residence. The age of 45 is filtered and converted into an age range of forties and the like. Only the age range and sex are registered.

Statistical data are registered in the archive database 24 in addition to the medical care data of the patient as results of the health checkup and complete medical checkup, the statistical data being obtained by statistically processing the medical care data of the patients in the hospital facilities 11. Examples of the statistical data include distribution of the patients of various symptoms, such as a lung cancer, diabetes and the like, for various age ranges, and the number data of the number of the patients of the use of particular drugs for various symptoms (for example, the number of patients of the lung cancer and of the use of a drug A). The medical care data of the patients are converted to the statistical data on a condition of patient consent of the respective patients, and registered in the archive database 24.

As will be described later, the management server apparatus 16 relocates part of the confidential data in the server database to the archive database 24 assuming that predetermined conditions are met. Specifically, the addition or updating of the confidential data is monitored. Assuming that a problem event of exacerbation of a patient occurs and assuming that a patient consent is obtained, then part of the medical care data registered as the confidential data is relocated to the published data.

It is socially known according to survey that there are numerous patients having wish for beneficial contribution in utilization of their medical care data for the secondary use, for example, research purposes in the medical field in view of numerous patients in the world and innovation in medical procedures. Patients with severity after exacerbation of their symptoms are likely to have much concern about the beneficial contribution. In the present invention, the management server apparatus 16 operates upon occurrence of a problem event of exacerbation of symptoms of patients, sends a request message for patient consent for the secondary use of medical care data for partial relocation to the published form of the medical care data by meeting their concern, and performs the relocation of the medical care data to published data.

Examples of the problem events are progress in the cancer stage from stage 3 to stage 4, occurrence of adverse effect of a drug for a cancer, and the like.

Each one of the HIS 14, the medical support server apparatus 12, the management server apparatus 16 and the client terminal apparatus 17 is constituted by a computer and programs installed therein. Examples of the computer are a personal computer, server computer, workstation and the like. The programs include control programs and application programs. The control programs are an Operating System (OS) and the like. The application programs are client programs, server programs and the like.

In FIG. 5, computers constituting the HIS 14, the medical support server apparatus 12, the management server apparatus 16, the client terminal apparatus 17 and the like are basically constructed equally. Each of the computers includes a non-transitory storage medium 30 or storage device, a non-transitory memory 31, a CPU 32 (central processing unit), a communication interface 33, a display panel 34 and a user input panel 35. A data bus 36 connects those circuit devices with one another.

The storage medium 30 is a hard disk drive incorporated in the computer, or connected to the computer by a cable, network or the like. Also, the storage medium 30 may be a disk array having plural hard disk drives. The storage medium 30 stores a control program and various application programs such as the Operating System (OS), and display page data for control pages associated with the programs.

The memory 31 is a working memory with which the CPU 32 performs tasks. The CPU 32 loads the memory 31 with the programs stored in the storage medium 30, and controls various circuit devices in the computer by performing the tasks according to the program.

The communication interface 33 is a network interface for communication with the WAN 13, or with the LAN in the hospital facilities 11. The display panel 34 displays a control page where an input action can be performed by use of the user input panel 35, such as a mouse, keyboard and the like. The control page has a function according to the GUI (graphical user interface).

Figure 6:
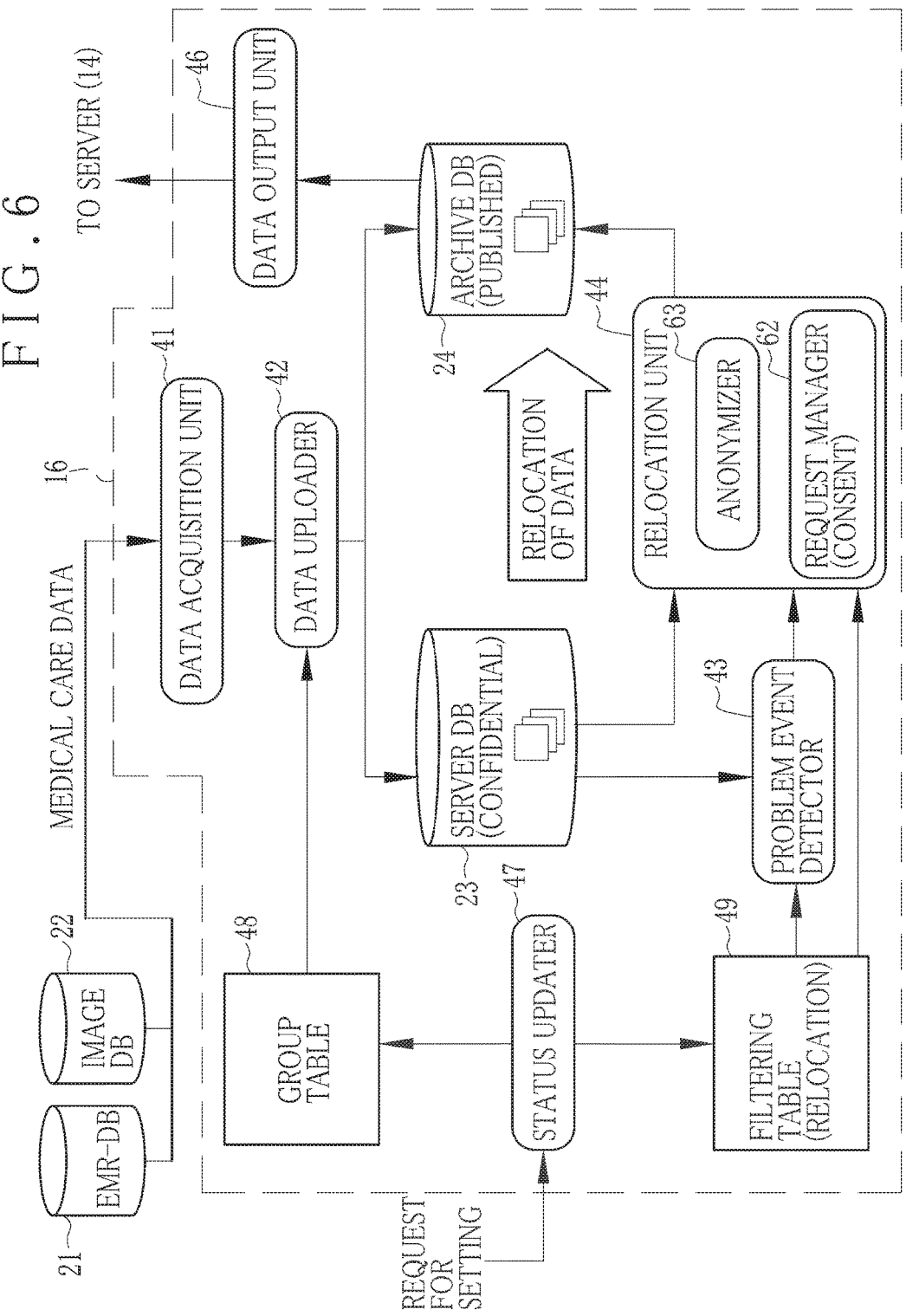
FIG. 6 is a block diagram schematically illustrating circuit devices in the management server apparatus.

In the computer for the management server apparatus 16, a control program for the information management apparatus is installed in the storage medium 30 as an application program. In FIG. 6, the control program is run in the CPU 32 of the management server apparatus 16 to establish a data acquisition unit 41, a data uploader 42 or registration unit, a problem event detector 43 or exacerbation event detector, a relocation unit 44 or transition unit, a data output unit 46 or data provider, and a status updater 47.

The data acquisition unit 41 performs periodic access to the EMR database 21 and the image database 22, and acquires medical care data. The data uploader 42 classifies the medical care data into confidential data only for a primary use of medical care of the patient, and published data of a published form for a secondary use other than the primary use. The confidential data is registered in the server database 23. The published data is registered in the archive database 24.

The data acquisition unit 41 performs access to the EMR database 21 and the image database 22 at a predetermined schedule, for example, one time per one day, and acquires medical care data after the addition or updating. It is possible for the HIS 14 to generate a message of updating at each time of updating the EMR database 21 or the image database 22, so that the data acquisition unit 41 can receive the message and acquire the medical care data, instead of the periodic access. The medical care data acquired by the data acquisition unit 41 is transmitted to the data uploader 42.

Figure 7:
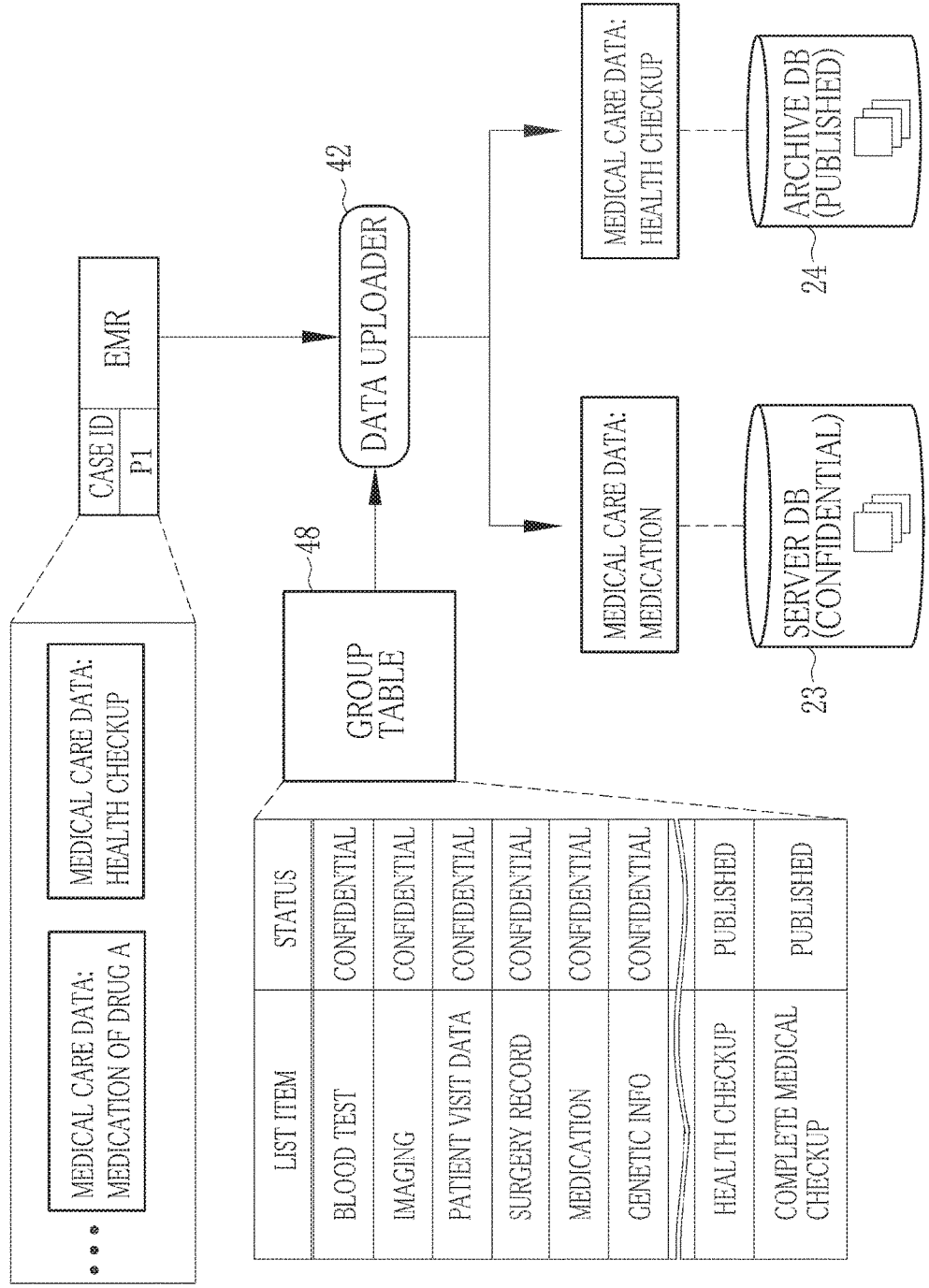
FIG. 7 is a block diagram schematically illustrating a data uploader.

In FIG. 7, a group table 48 is referred to by the data uploader 42, which classifies the obtained medical care data into published data and confidential data. The group table 48 is stored in the storage medium 30. Group addresses of the medical data are determined in the group table 48 a group of the published data and a group of the confidential data for respective list items of the medical care data.

In the embodiment, list items of the results of the health checkup and the complete medical checkup are set as published data. However, other list items are set as confidential data, including a blood test, imaging, progress record, surgery record, medication, genetic information. The data uploader 42 refers to the group addresses in the group table 48 for the respective list items of the acquired medical care data. For example, a group address of classification for the medication is confidential data, to register the medical care data to the server database 23. In contrast, a group address of classification for the health checkup is published data, to register the medical care data to the archive database 24.

Figure 8:
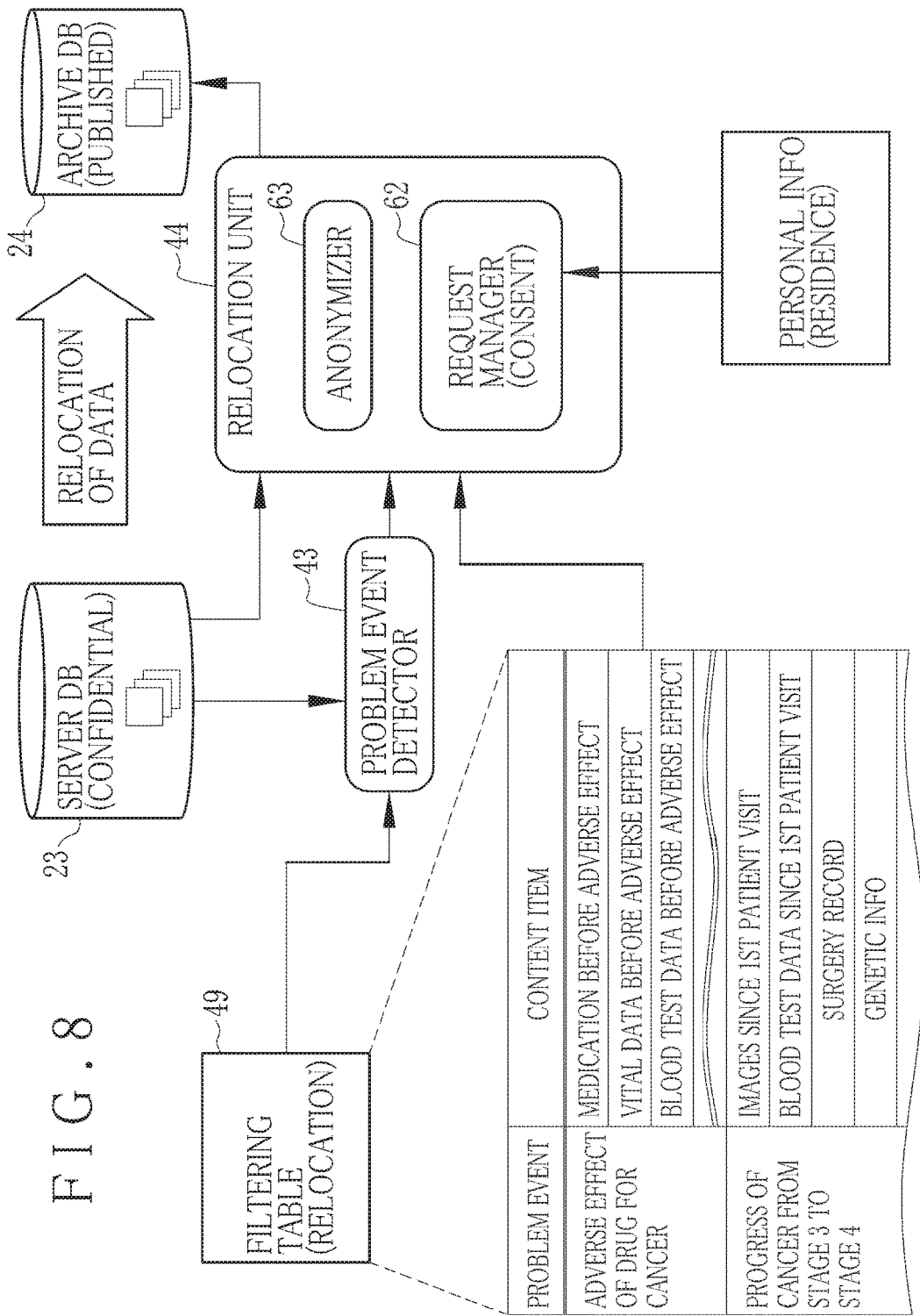
FIG. 8 is a block diagram schematically illustrating a problem event detector and a relocation unit.

In FIG. 8, the problem event detector 43 monitors added or updated confidential data in the server database 23, and checks whether a problem event of exacerbation of the progress of the patient has occurred. A filtering table 49 (relocation table) is referred to by the problem event detector 43 for checking the problem event. The filtering table 49 is a data table containing predetermined types of problem events, and content items (relocation items) in association with the types of the problem events. The content items are information items for relocation from the confidential data to the published data. The filtering table 49 is stored in the storage medium 30.

Types of the problem events are determined according to a symptom name, symptom progress, disease period and the like. A data table for the patient P1 contains examples of the types of the problems events, such as "occurrence of adverse effect of a drug for a cancer", and "progress in the cancer stage from stage 3 to stage 4".

While "occurrence of adverse effect of a drug for a cancer" is set as a problem event to be detected, the problem event detector 43 performs access to the server database 23 to read medical care data related to the drug administration, and checks whether the test value is in an unusual range, and whether the occurrence of the adverse effect has been recorded by a doctor according to record areas of findings and diagnosis in the EMR. Also, an event of "progress in the cancer stage" is a problem event of the exacerbation of the patient. The problem event detector 43 refers to the record areas of the findings and diagnosis in the EMR, and confirms the record of the relevant problem event.

Also, the types of the problem events include "change in the test value in a direction to exacerbation". Then the problem event detector 43 checks that the test data is in a reference range of a problem, or checks that a relevant description is contained in the field for findings in the progress note, so as to perform judgement of the type of the problem event.

Assuming that the problem event is "adverse effect of drug for a cancer", examples of content items set for a respective type of the problem events are drug administration, vital data, blood test data and the like before and after an occurrence of the adverse effect. Assuming that the problem event is "progress in the cancer stages", examples of content items are diagnostic images and blood test data recorded since the first patient visit, and surgical information and genetic information.

Types of the problem events include symptom types. List items of medical care data with preference for publication are changeable according to the symptom types in view of benefits in the secondary use. For example, a published form of genetic information in relation to a symptom with close relationship with genetic information is highly required, for the reason of benefits for the secondary use. However, a published form of genetic information in relation to a symptom without close relationship with genetic information is slightly required. Content items are information determining which ranges of list items of medical care data should be published. In the filtering table 49, content items are selectable for types of the problem events, so that suitable content items can be set according to requirement for the respective types of the problem events.

Also, it is possible with the filtering table 49 to protect privacy of the patients suitably by setting content items for the types of the problem events. Specifically, the genetic information is set as a content item only for a symptom with strong connection to the genetic information, but set not as a content item for a symptom with weak connection to the genetic information, because of close relationship to identifying the respective patients. In short, the range of the openness is preferably minimized, in view of protecting the privacy.

The problem event detector 43 monitors confidential data for respective patients, checks addition or updating of confidential data and selected types of problem events for the patient in the filtering table 49, and detects occurrence of a problem event. Upon detecting the occurrence, the problem event detector 43 informs the relocation unit 44 of the occurrence.

The relocation unit 44 upon receiving information of occurrence of a problem event starts preparatory processing for relocating part of confidential data to published data as content items. The preparatory processing is for obtaining patient consent from a patient in order to relocate the confidential data in a published form. In the embodiment, a request manager 62 for patient consent or approval processor (activation processor) is incorporated in the relocation unit 44, and performs processing of approval request by way of the preparatory processing. The processing of approval request is transmission of a request message to the patient to ask for the patient consent in relation to part of the confidential data as content items.

The request manager 62 creates a message text containing a content item set in the filtering table 49, a request message for requesting patient consent for a published form (open archival) related to the content item, and a message containing a description of purposes of the published data and anonymization of the content item. The request manager 62 reads a mail address of the patient or other information of an addressee from the personal information, and transmits the message text to the mail address.

The relocation unit 44 upon receiving the patient consent for public use in the request manager 62 detects a flag signal generated in the request manager 62, to activate the relocation processing. The relocation unit 44 starts the relocation processing. In the relocation from the confidential data to the published data, anonymization is performed. An anonymizer 63 (filtering device) is incorporated in the relocation unit 44 for anonymizing data.

The anonymization is filtering in which medical care data of respective patients is maintained but information identifying the patients is anonymized or removed in confidential data to be relocated. Note that statistical processing of statistical data from medical care data of plural patients can remove the information identifying the patients. However, the anonymization is different from the statistical processing, because the medical care data is filtered while the form (content information) of the medical care data is maintained.

Even for the purpose of using the medical care data in the published form, privacy must be protected. No personal names of patients are required for the secondary use. Thus, the medical care data are anonymized in the anonymization in the relocation to the published data.

In general, medical care data for the secondary use is valuable according to highness in the information amount of attribute data of patients. Thus, the anonymizer 63 performs the anonymization in a form of maintaining part of attribute data, such as age, blood type, medical history and genetic information other than the patient name, to ensure the benefits of the medical care data in the secondary use.

Figure 9:
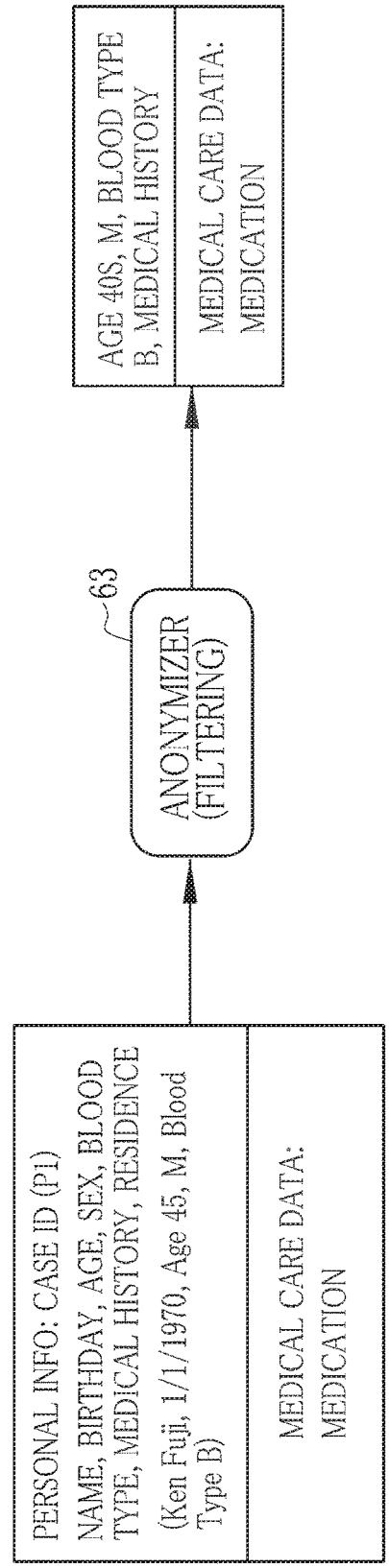
FIG. 9 is a data chart illustrating anonymization of data in an anonymizer.

In FIG. 9, the anonymizer 63 in the embodiment performs anonymization of the medical care data of the patient of interest, namely, deletes the name and residence (address) of the patient, and converts his or her age into an age range. Description of the anonymization is included in notice for the patient consent (approval), so that the patient can give the patient consent after confirming the use of the anonymization.

In FIG. 6, the data output unit 46 receives a request from the WAN 13 through for information distribution, and provides published data in the archive database 24 responsively. The data output unit 46 responds to a search query from the request, such as a symptom name, drug name and the like, and reads out the published data in association with the search query for the information distribution. To this end, HTTP (Hypertext Transfer Protocol) as a well-known communication protocol is used for the distribution.

Furthermore, it is possible periodically to supply the published data to the medical research facility 26 and the like collectively. To this end, a file transfer protocol, such as FTPS (File Transfer Protocol over SSL/TLS) and the like well-known technically can be used to distribute the published data automatically. Also, an electronic mail can be used in place of the file transfer protocol. The supplied published data from the medical support server apparatus 12 is distributed to the hospital facilities 11 and the medical research facility 26 for the secondary use.

The status updater 47 sets and varies the content information in the group table 48 and the filtering table 49. An input action performed at a console unit or user input interface for the management server apparatus 16 is considered to set and modify the group table 48 and the filtering table 49. Note that other inputs can be used for setting the group table 48 and the filtering table 49, for example, inputs received at the client terminal apparatus 17 and transmitted by the LAN, instead of using the console unit of the management server apparatus 16.

Figure 10:
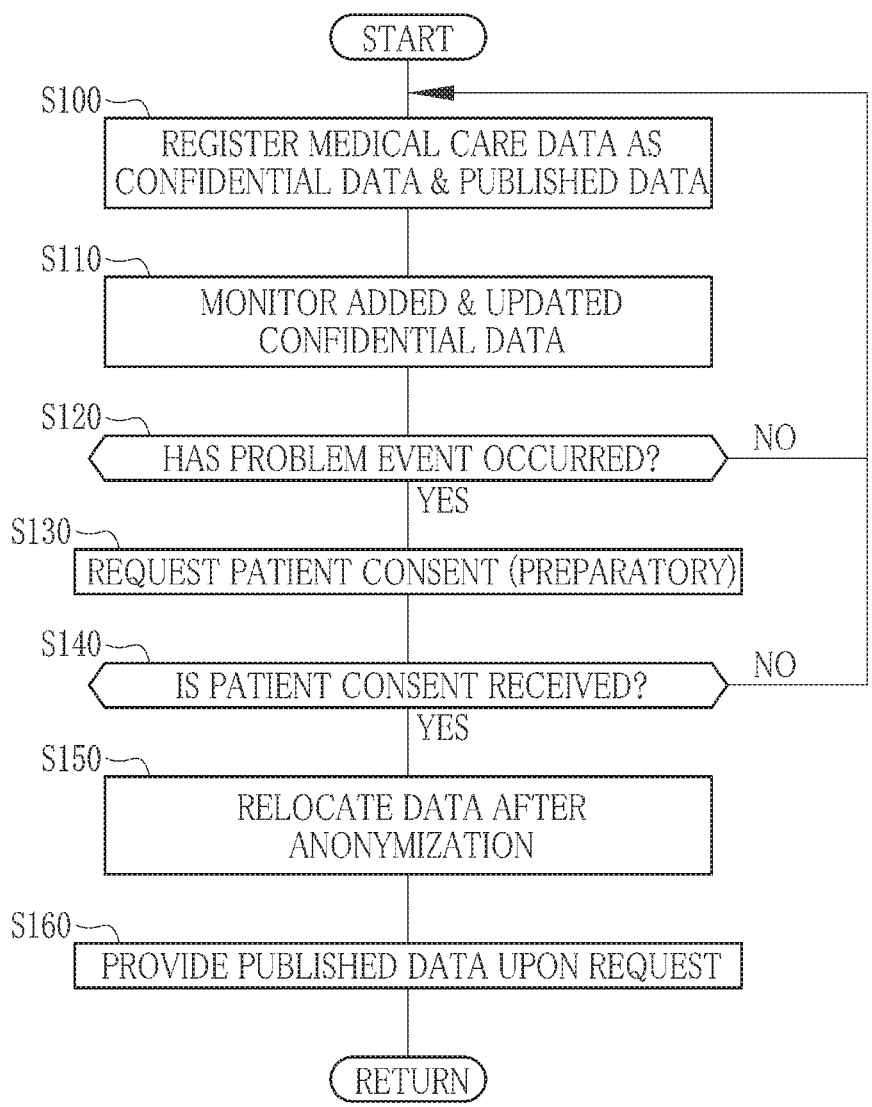
FIG. 10 is a flowchart illustrating information management in the management server apparatus.

The operation of the above embodiment is described by referring to a flow in FIG. 10. The data acquisition unit 41 in the management server apparatus 16 performs access to the EMR database 21 and the image database 22 and acquires medical care data. The data uploader 42 classifies the medical care data into confidential data only for the primary use and published data for the secondary use (open archival), which are registered in respectively the server database 23 and the archive database 24 in a step S100. In FIGS. 4A and 4B, the archive database 24 in an initial step stores only results of health checkup and complete medical checkup and statistical data. Remaining part of the medical care data are registered in the server database 23.

The data acquisition unit 41 updates the server database 23 in response to data addition or data updating of the EMR database 21 or the image database 22. The problem event detector 43 monitors medical care data (confidential data) in the server database 23 to be added or updated in a step S110. It is checked in a step S120 whether a problem event determined in the filtering table 49 has occurred according to the added or updated medical care data. While there is no problem event, the problem event detector 43 continues monitoring (no in the step S120). Assuming that it is judged that a problem event has occurred (yes in the step S120), the problem event detector 43 informs the relocation unit 44 of the occurrence. The relocation unit 44 responsively starts preparatory processing in a step S130.

The request manager 62 in the relocation unit 44 creates a message containing a content item among the confidential data, a request message for requesting patient consent for a published form (open archival) related to the content item, and a description of purposes of publishing medical care data and anonymization of the content item. Then the request manager 62 sends the message to the patient in the step S130.

The request manager 62 judges that no patient consent is acquired (no in a step S140) assuming that no patient consent is received from the patient, or assuming that refusal is received from the patient for refusing the published form. However, the request manager 62 judges that a patient consent is acquired (yes in the step S140) in case the patient consent is received. The request manager 62 generates a flag signal to activate the relocation in the relocation unit 44. Then the relocation unit 44 filters and anonymizes confidential data of content items, to relocate the confidential data to the published data after the anonymization. The published data is registered in the archive database 24. Thus, the relocation is completed in a step S150.

The data output unit 46, upon receiving the request from the medical support server apparatus 12, provides the published data registered to the archive database 24 by information distribution to the medical support server apparatus 12, in a step S160. The published data is used for the secondary use by the information distribution to the medical research facility 26 or the hospital facilities 11 from the medical support server apparatus 12. The management server apparatus 16 repeats the above tasks until the end of the startup.

Figure 11:
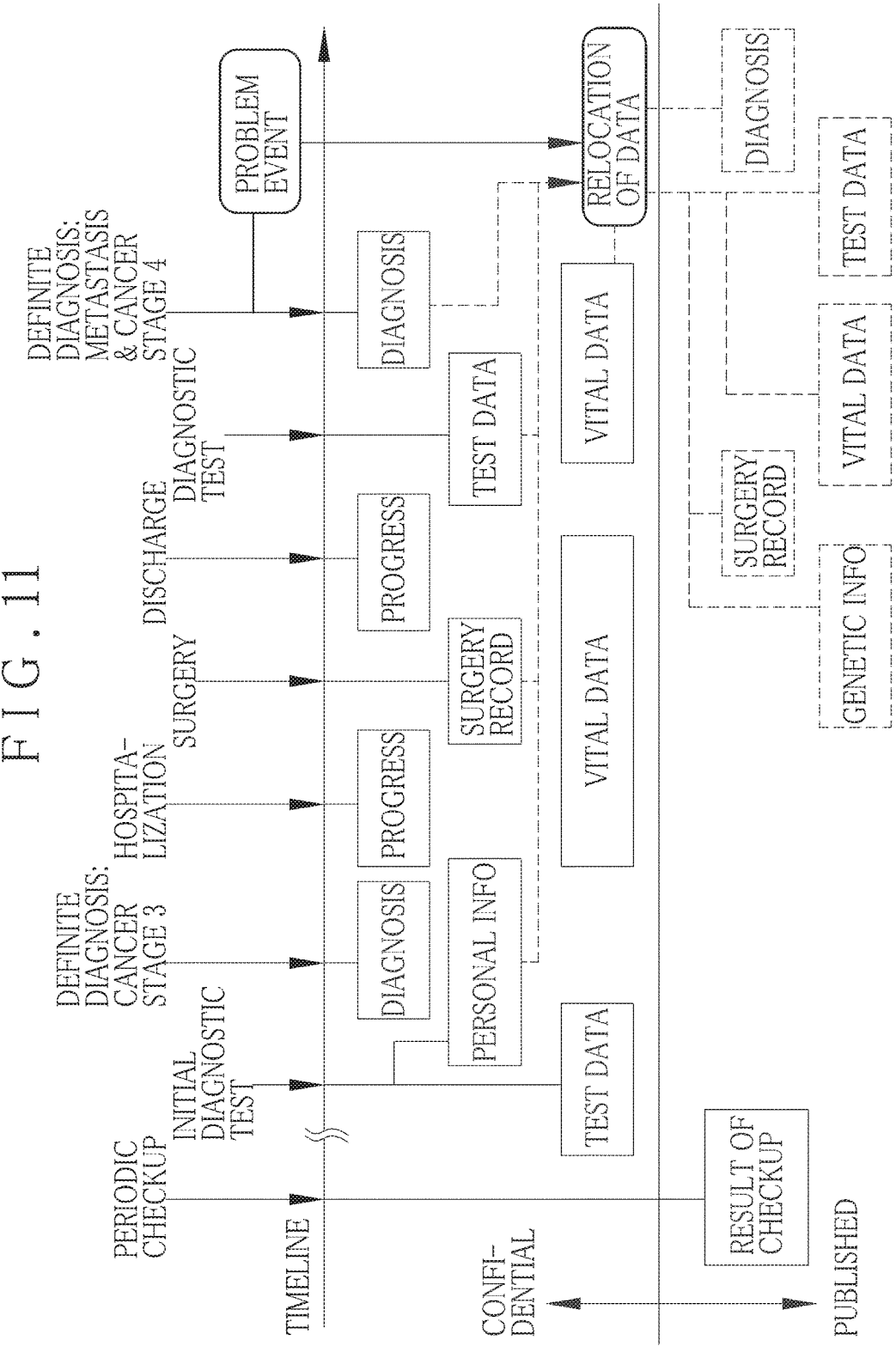
FIG. 11 is a timing chart illustrating relocation from confidential data to published data.

In FIGS. 11 and 12, flows of handling medical care data are illustrated, inclusive of a step of storing the medical care data in the server database 23 in the progress of medical care, and a step of relocating part of the confidential data to published data.

In FIG. 11, an example of a problem event is progress of a cancer from stage 3 to stage 4. For example, the patient of FIG. 11 was checked in periodic health checkup so as to discover a disease. He or she was checked more precisely in medical checkup so that definite diagnosis of the cancer of stage 3 was performed. Then the patient was hospitalized, underwent surgery of tumorectomy, and then discharged. He or she received a follow-up test for observing the progress in prognosis. However, there was a new definite diagnosis of metastasis of the cancer and progress of from stage 3 to stage 4.

Then the first precise checkup is the first patient visit after the periodic health checkup. An EMR is drafted and produced. In the course of succeeding medical care, various medical care data are collected and input to the EMR, including a result of the definite diagnosis, patient visit data, surgery record, vital data after the hospitalization. As the medical care data are stored to the EMR database 21 or the image database 22, the management server apparatus 16 registers the medical care data to the server database 23 as confidential data.

Assuming that a result of health checkup before a first patient visit is provided from a patient, the result is input to the EMR. Assuming that a patient consent is obtained, the result is registered as published data. It is possible to register results of health checkup of still earlier dates as published data in the case of provision from the patient. Medical care data of the health checkup or complete medical checkup are registered in an anonymous form after deleting the name and the like of the patient as described with FIG. 4B.

Assuming that optional medical data or healthcare record is provided by each patient, the healthcare record can be input to the EMR, such as changes in the blood pressure, body temperature or the like of daily health checkup before the first patient visit.

In case the metastasis of the cancer and the progress from stage 3 to stage 4 of the cancer are detected, then occurrence of a problem event is judged as information of exacerbation of the symptom in the patient body. Then the management server apparatus 16 requests and acquires patient consent, and relocates (filters) part of the confidential data to published data, which is registered in the archive database 24. In FIG. 8, the filtering table 49 has content items for the "progress in the cancer stage", such as a diagnostic image, blood test data, surgical information, genetic information and the like. The confidential data is relocated to the published data and registered in the archive database 24.

In the embodiment of FIG. 12, adverse effect is created by the drug administration which is used for treatment of a cancer. In the same manner as FIG. 11, a problem in a patient is detected in the health checkup. He or she is hospitalized after receiving a definite diagnosis of the cancer of stage 3.

Also, an EMR is newly created at the time of a first patient visit of a patient, because first checkup with precision after the periodic healthcare check is the first patient visit, in the same manner as the example of FIG. 11. Various medical care data are collected serially according to a succeeding process of the medical care, and input to the EMR, the medical care data including test data of diagnostic tests, results of final diagnosis, patient visit data, record of drug administration, and vital data after hospitalization. The medical care data are stored in the EMR database 21 or the image database 22, and registered to the server database 23 as confidential data by the management server apparatus 16.

In the patient of FIG. 12 after treatment of the drug administration, adverse effect of the drug has occurred. The management server apparatus 16 judges that the adverse effect of the drug is a problem event. After a patient consent is acquired, the management server apparatus 16 relocates part of the confidential data to published data, which is registered in the archive database 24. In FIG. 8, content items are set in the filtering table 49 for the problem event of "occurrence of adverse effect of a drug for a cancer", including the medication, vital data, blood test data and the like. The confidential data is relocated to published data, which is registered in the archive database 24.

Published data registered in the archive database 24 is supplied to the medical support server apparatus 12 external from the hospital facilities 11, so that the medical support server apparatus 12 allows the hospital facilities 11 and the medical research facility 26 to use the published data for the secondary use.

In short, the management server apparatus 16 starts the preparatory processing to relocate part of confidential data to published data upon occurrence of a problem event of exacerbation of a disease of a patient, namely, upon occurrence of severity in the disease in progress of a disease period, or upon occurrence of adverse effect of the drug administration.

As described heretofore, the medical care data of the patients are remarkably more valuable in the secondary use (open archival) for researching clinical cases than statistical data of which differences between the patients are removed. Medical care data as clinical cases is valuable according to highness of clarity of attribute data of patients, such as a sex, age with precision, blood type, genetic information and medical history. However, privacy of the patient is likely to be revealed according to the clarity of the attribute data of the patients. In general, patients aware of his or her cases for the benefits in the medical research have been increased today, as the use of the medical care data can be enhanced in the research with priority over the protection of their privacy.

The management server apparatus 16 activates the relocation processing to relocate part of the confidential data to the published data upon generation of a flag signal which expresses reception of a patient consent related to publishing medical care data after a problem event. Thus, it is possible to support the secondary use of the medical care data by considering the personal wish of the patients. In short, the time point of occurrence of a problem event is suitable for the shift of the confidential data to the published data for the secondary use in view of the personal wish of the patients for the secondary use of their medical care data.

Then preparatory processing for the relocation is started upon occurrence of the problem event. A request message is sent to the patient to ask for a patient consent to the published form.

It is possible suitably to meet the wish for beneficial contribution of a patient for the public use of the medical care data at a suitable time point. Thus, the open archival and research use of the medical care data can be encouraged. The medical care data can be utilized for the secondary use, which can be supported on the basis of the patient consent of the patient for the public use of the medical care data.

In future, the use of medical care data of a great amount will be increased as big data for the secondary use. It is necessary to collect and accumulate valuable medical care data.

The management server apparatus 16 smoothly collects and accumulates medical care data for the secondary use with high effects owing to reception of the patient consent.

In the embodiment, part of the confidential data is relocated to the published data by filtering upon occurrence of a problem event. However, all of the confidential data can be relocated to the published data. However, the partial relocation of the confidential data by filtering required for the type of the problem event at each time of occurrence of the problem event is effective in view of protecting privacy of the patients.

In the preparatory processing, it is possible rapidly to check whether respective patients give patient consent, because a request for patient consent is transmitted to the patients in relation to part of confidential data as content items for published data.

In the preparatory processing for the relocation, it is possible to transmit an alert message to a medical professional to encourage acquisition of a patient consent for the public use, in place of transmitting a request message to the patient to ask for the patient consent. For example, the alert message includes description of occurrence of a problem event in a certain patient, description of possibility of publishing part of the confidential data of the patient, and description of requirement of acquiring a patient consent for a published form of the data. The medical professional upon receiving the alert message talks to the patient directly or by telephone, and requests him or her to sign the patient consent for the published form of the data. Upon acquisition of the patient consent, information of the patient consent is input to the management server apparatus 16. A flag signal of the patient consent is generated, so as to activate and perform the relocation.

Publishing medical care data is a delicate issue related to privacy of the patient. A request for a patient consent must be transmitted with much care. Although the preparatory processing is the approval request or transmitting a direct request to a patient, another example of the preparatory processing can be an alert message or reminding message of encouragement to a medical professional for requesting a patient consent. Furthermore, two or more examples of the preparatory processing for the purpose of the relocation can be combined for use.

Also, the relocation unit 44 performs the relocation processing upon receiving the notice of the patient consent from the patient. It is possible to confirm the wish for beneficial contribution of the patient immediately before storage in a published form. Protection of the privacy of the patient can be ensured reliably.

In the embodiment, the medical care data is anonymized to relocate the confidential data to the published data. However, anonymization of medical care data can be omitted assuming that a patient gives a patient consent to omission of the anonymization. However, omission of the anonymization in an excessive form may lead to unwanted spread of personal information. Thus, it is preferable to delete at least a name of the patient, to pseudonymize the name, or to perform anonymization of a suitable form.

In the embodiment, the WAN 13 is used for the data output unit 46 to provide the published data. However, it is possible to store published data in a storage medium, such as a USB memory (Universal Serial Bus memory), DVD (Digital Versatile Disc) and the like, for the purpose of providing the published data. The data output unit 46 is not necessary in the use of the storage medium. However, the data output unit 46 can be preferably used, because the provision of the data with the WAN 13 is performed more simply and more easily than the provision by use of the storage medium.

[Second Embodiment]

Figure 13:
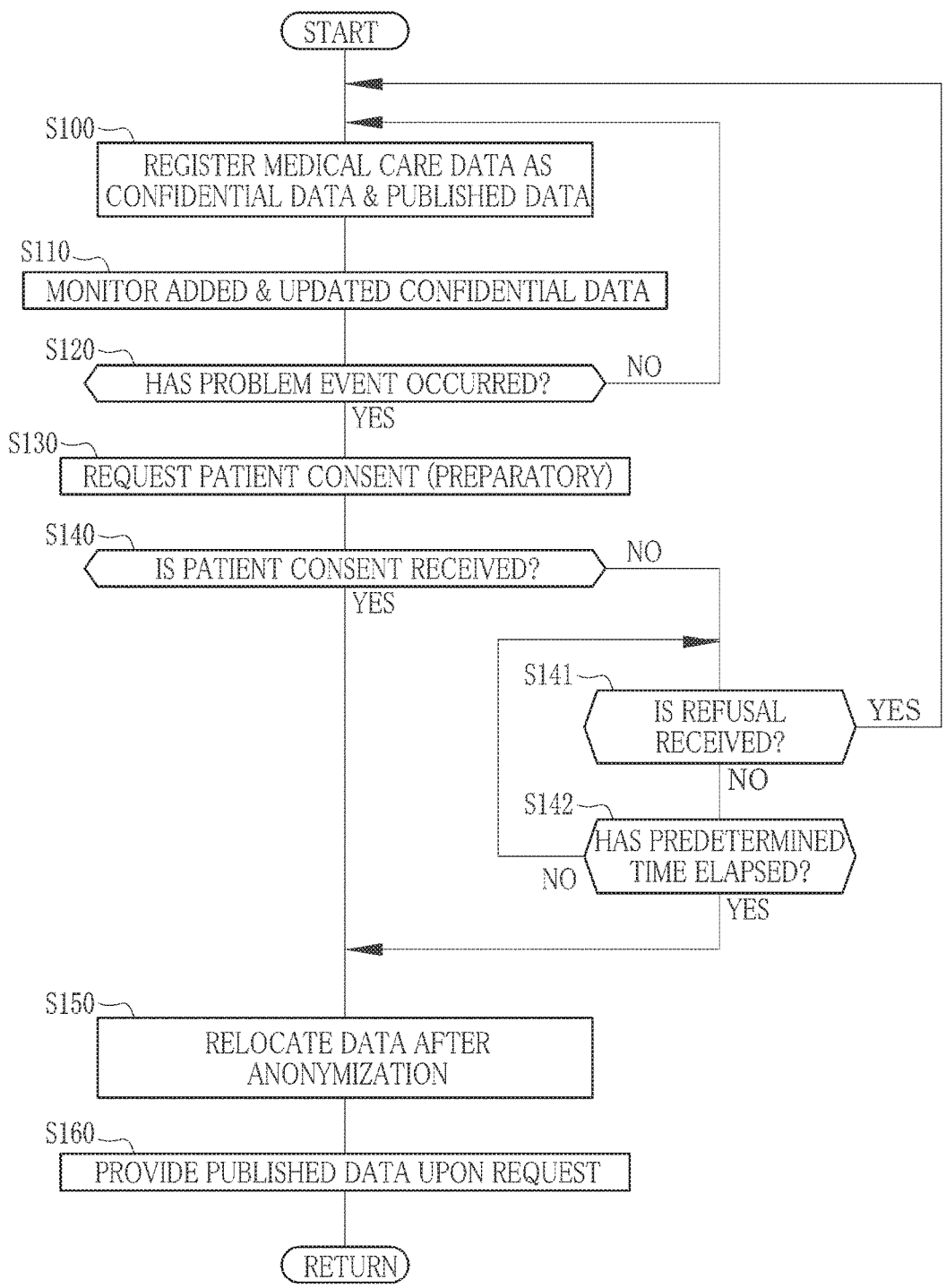
FIG. 13 is a flow chart illustrating a second preferred embodiment.

Checking of a patient consent in the request manager 62 in the first embodiment is exactly according to reception of the patient consent from the patient. However, it is possible to perform relocation of data by activation with a flag signal as illustrated in FIG. 13.

Assuming that no consent is received even upon lapse of a predetermined time after transmission of a request, then the processing of the relocation is performed under a condition of supposition of probable consent. Let the request manager 62 not receive a consent after transmission of the request (no in the step S140). Assuming that a state without receiving a refusal (no in a step S141) is continued for a predetermined time (yes in a step S142), then the request manager 62 performs the processing of the relocation with the supposition of probable consent from the patient. In short, reception of a presumed consent (provisional consent) is performed upon a lapse of the predetermined time of continuing an unchanged state without receiving a consent or refusal. In case a predetermined time elapses after transmitting a request according to measurement with a timer, a flag signal is generated automatically, so that the relocation is activated.

A certain patient may forget sending of a patient consent inadvertently assuming that he or she wishes to send one. There arises a problem in inefficiency in accumulating published data according to highness in the number of such inadvertent patients. Thus, the reception of a presumed consent of the patient consent is effective in developing the accumulation of the published data. It is noted that notification should be made previously to patients in that the reception of a presumed consent of a patient consent will be automatically performed upon lapse of a predetermined period without receiving a patient consent.

[Third Embodiment]

Figure 15:
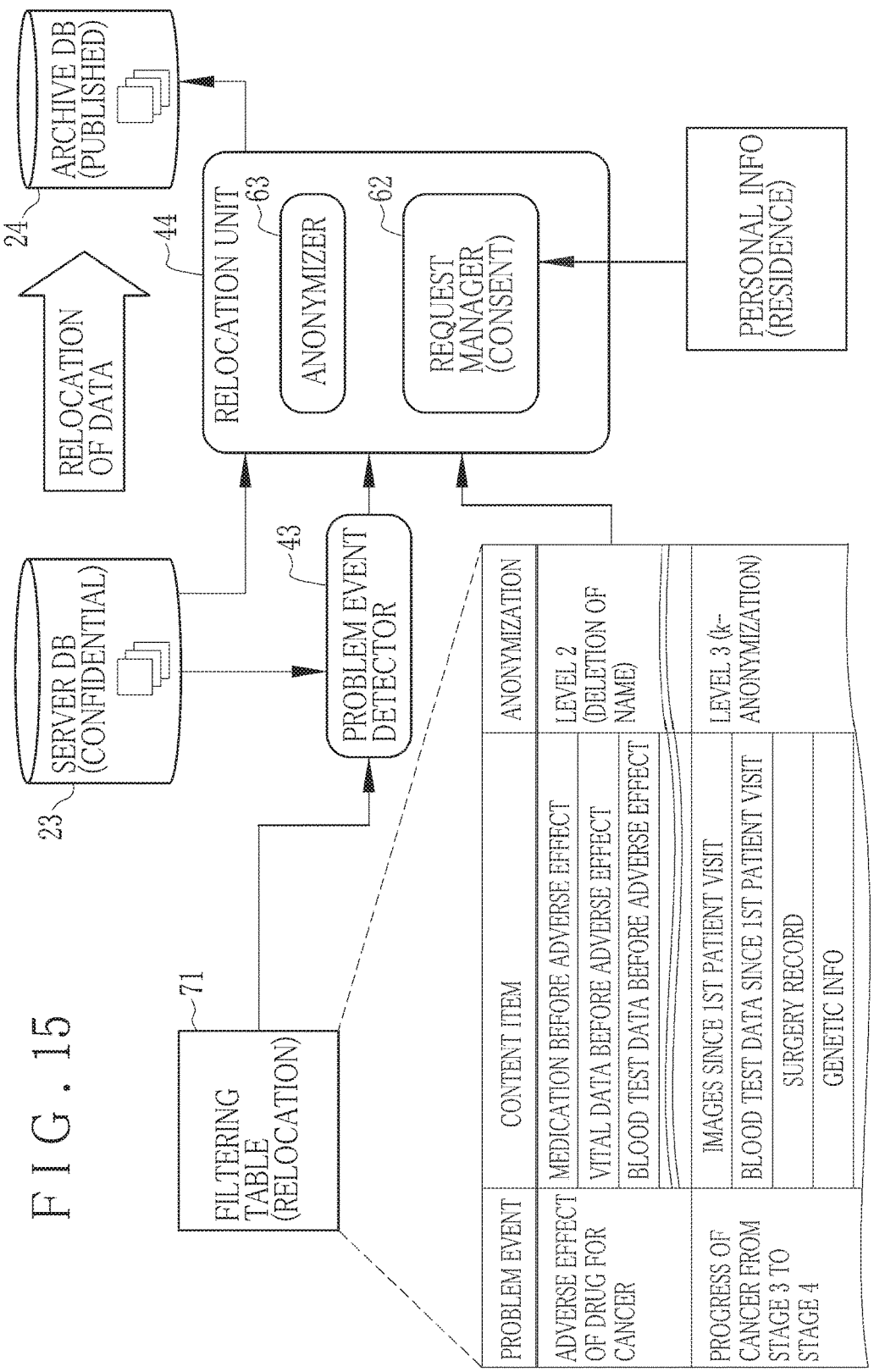
FIG. 15 is a block diagram schematically illustrating the third preferred embodiment.

In FIGS. 14 and 15, reference information of the anonymization is variable in plural levels of the anonymization in the anonymizer 63, the levels being associated with levels of difficulties in identifying the patient. A data amount of attribute data (age, blood type, medical history and the like) of the patient after the anonymization is small according to highness of the level of the anonymization, to increase difficulty in identifying the patient. In contrast, a data amount of attribute data of the patient after the anonymization is large according to lowness of the level of the anonymization, to facilitate identification of the patient.

For example, it is possible for the anonymizer 63 to perform the anonymization in plural levels of levels 1, 2 and 3. The levels 1, 2 and 3 are listed in an increasing sequence of highness.

The level 1 is a method of anonymization, so-called connection anonymization, in which true names of the patients are deleted from the confidential data, and pseudonyms of a sign or number are allocated to the confidential data, of which a mapping table between the pseudonyms and the true names is stored. In case of requirement, the patients may be identified. The anonymization level of the level 1 is the lowest, as the access to the mapping table easily enables identification of patients.

The level 2 is a method of anonymization by deleting a name of the patient. The anonymization level of the level 2 is higher than the level 1 because no mapping table is recorded. The level 3 is a method of k-anonymization. Let k patients or more have a common attribute in relation to medical care data of plural patients. After the use of the k-anonymization, it is possible by fine selection to detect a particular one of the k patients who has a selected one of the medical care data. However, no further fine selection is possible. The anonymization level of the level 3 is higher than the levels 1 and 2.

To set rare examples of data in a published form, for example, rare genetic information or rare medical history, k-anonymization is selected to avoid the use of level 1 or 2 of anonymization, which is insufficient for anonymization only by deleting the name of the patient. For example, the k-anonymization includes deletion of attribute data of less important genetic information and less important medical history in view of necessity of specific part of genetic information and specific part of medical history for the significance to the secondary use.

In FIG. 15, a filtering table 71 (relocation table) is illustrated in which anonymization levels are predetermined in a selectable manner in association with types of problem events. For example, let a type of a problem event be occurrence of adverse effect of a drug for a cancer. The anonymization level is set as the level 2. Let a type of a problem event be progress in the cancer stage. The anonymization level is set as the level 3, because genetic information is included in content items (relocation items). Furthermore, it is possible to set the anonymization levels changeable according to the content items (types of problem events to be relocated), in place of or in addition to the types of the problem events. Consequently, privacy of patients can be suitably protected according to the types of problem events and content items by the changeable structure of the anonymization levels.

[Fourth Embodiment]

Figure 16:
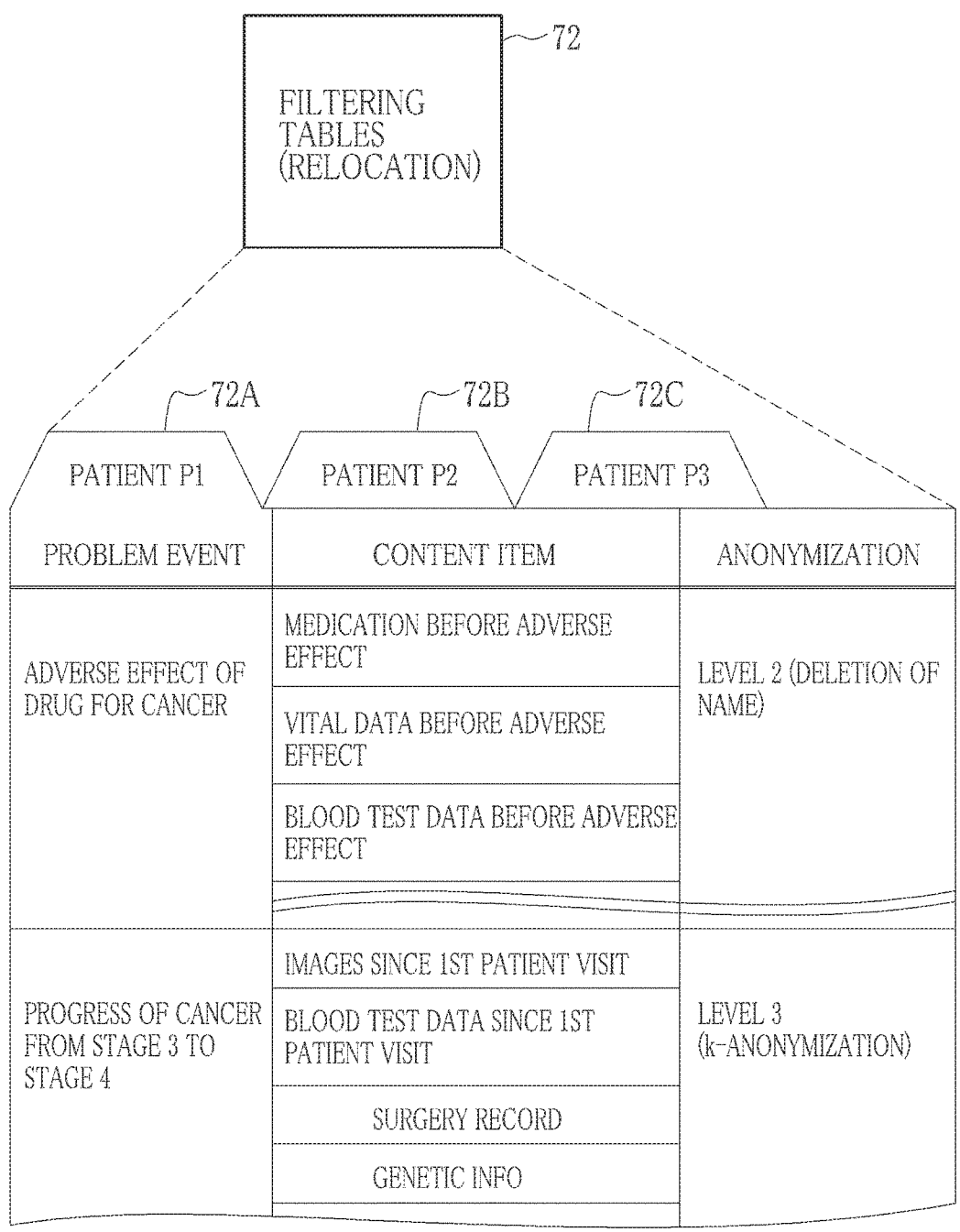
FIG. 16 is a data chart illustrating a fourth preferred embodiment.

In FIG. 16, content of the information is settable for respective patients in filtering tables 72 (relocation tables). The filtering tables 72 are filtering tables 72A, 72B and 72C (relocation tables) in association with the patients P1, P2 and P3. The content of the information is set in the filtering tables 72A-72C for the patients.

In the embodiment, the filtering tables 72A-72C are associated with respectively the patients. Various data can be settable for the patients, including a type of the problem events, content item and level of the anonymization. In general, the level of the anonymization to which each patient can give a consent is different between the patients in view of protecting their privacy. It is possible in the embodiment to set the medical care data in the published form by considering finely different state of the patient consent, because the types of the problem events can be determined with a fine adjustment.

Also, the group table 48 of FIG. 7 can be determined for the respective patients in the same manner as the filtering tables 72. Even in an initial step of registering medical care data in the management server apparatus 16, it is possible flexibly to handle a range of a published form of the medical care data and content items of the medical care data for the published form, according to the patient consent of individual patients.

[Fifth Embodiment]

Figure 17:
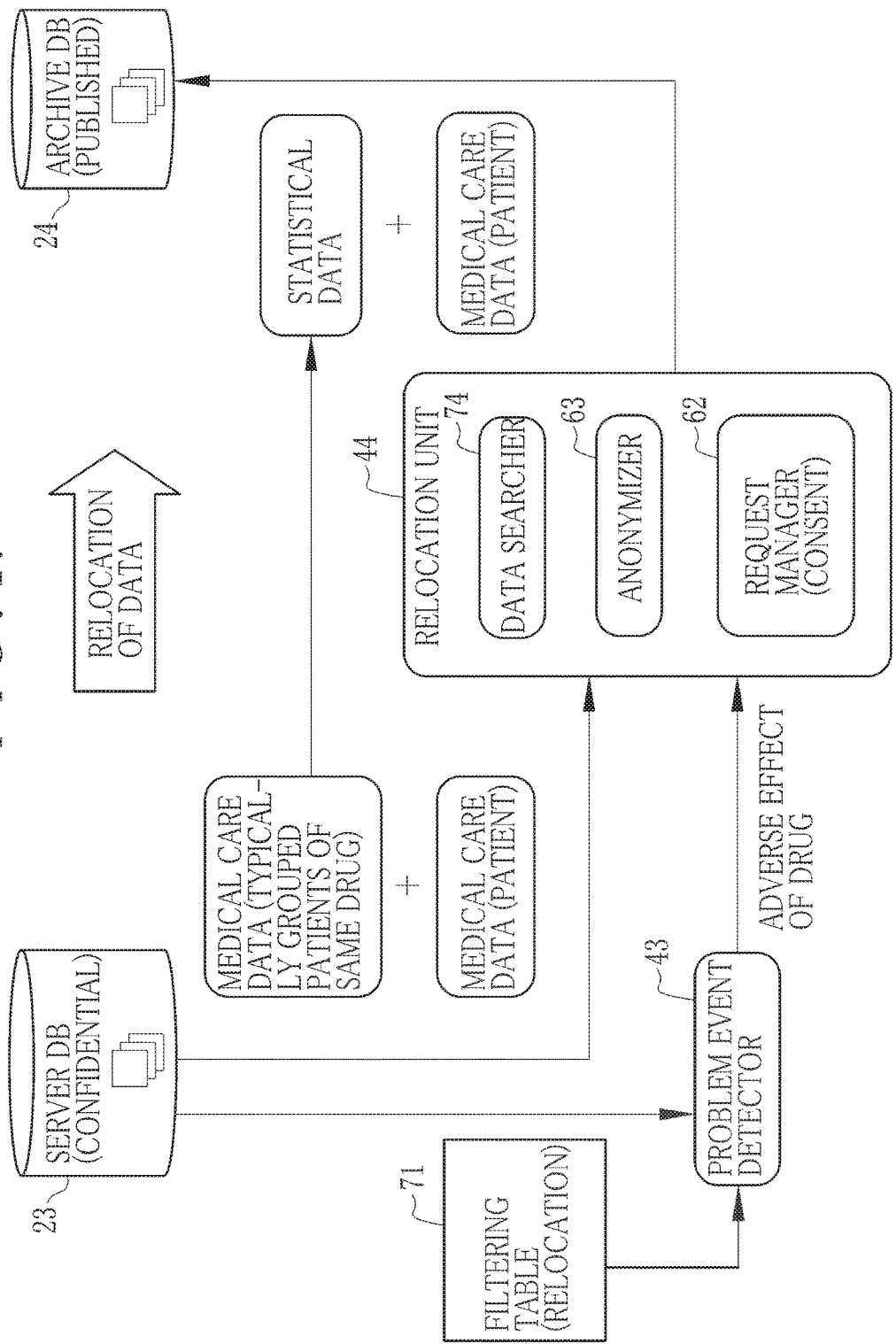
FIG. 17 is a block diagram schematically illustrating a fifth preferred embodiment.

In FIG. 17, statistical data of typically grouped patients can be published in the published form in addition to the medical care data of the patients of interest, on a condition of occurrence of adverse effect with drug administration as a problem event, the typically grouped patients being patients to whom the same drug have been administered.

In the embodiment, a data searcher 74 or data readout unit is incorporated in the relocation unit 44 in addition to the request manager 62 and the anonymizer 63. Assuming that the problem event detector 43 has detected occurrence of adverse effect of drug administration as a problem event, the data searcher 74 performs access to the server database 23 to search and detect medical care data of typically grouped patients to which the same drug has been administered among the patients other than the patient of interest of which the adverse effected has been detected.

The relocation unit 44 receives the medical care data of the plural typically grouped patients selectively detected by the data searcher 74, and produces statistical data in which each of the typically group patients is unidentifiable, by statistical processing of the medical care data. The relocation unit 44 functions as a statistical processor for changing data to statistical data. Also, the relocation unit 44 starts the preparatory processing for confidential data of the patients of interest after occurrence of a problem event, and relocates the statistical data to published data.

Thus, the statistical data of the typically grouped patients of the same drug can be referred to easily together with the medical care data of the patient of interest of occurrence of adverse effect after the drug administration. Factors of the adverse effect can be researched by comparison between the medical care data of the patient of interest and the statistical data related to the typically grouped patients of the same drug.

Note that the medical care data of typically grouped patients of the same drug other that the specific patients of interest have been converted to statistical data in which the patients are unidentifiable, so as to avoid violation of the privacy. It is additionally preferable to request and acquire patient consent in relation to the use of the statistical data for the purpose of ensured protection of privacy.

[Sixth Embodiment]

Figure 18:
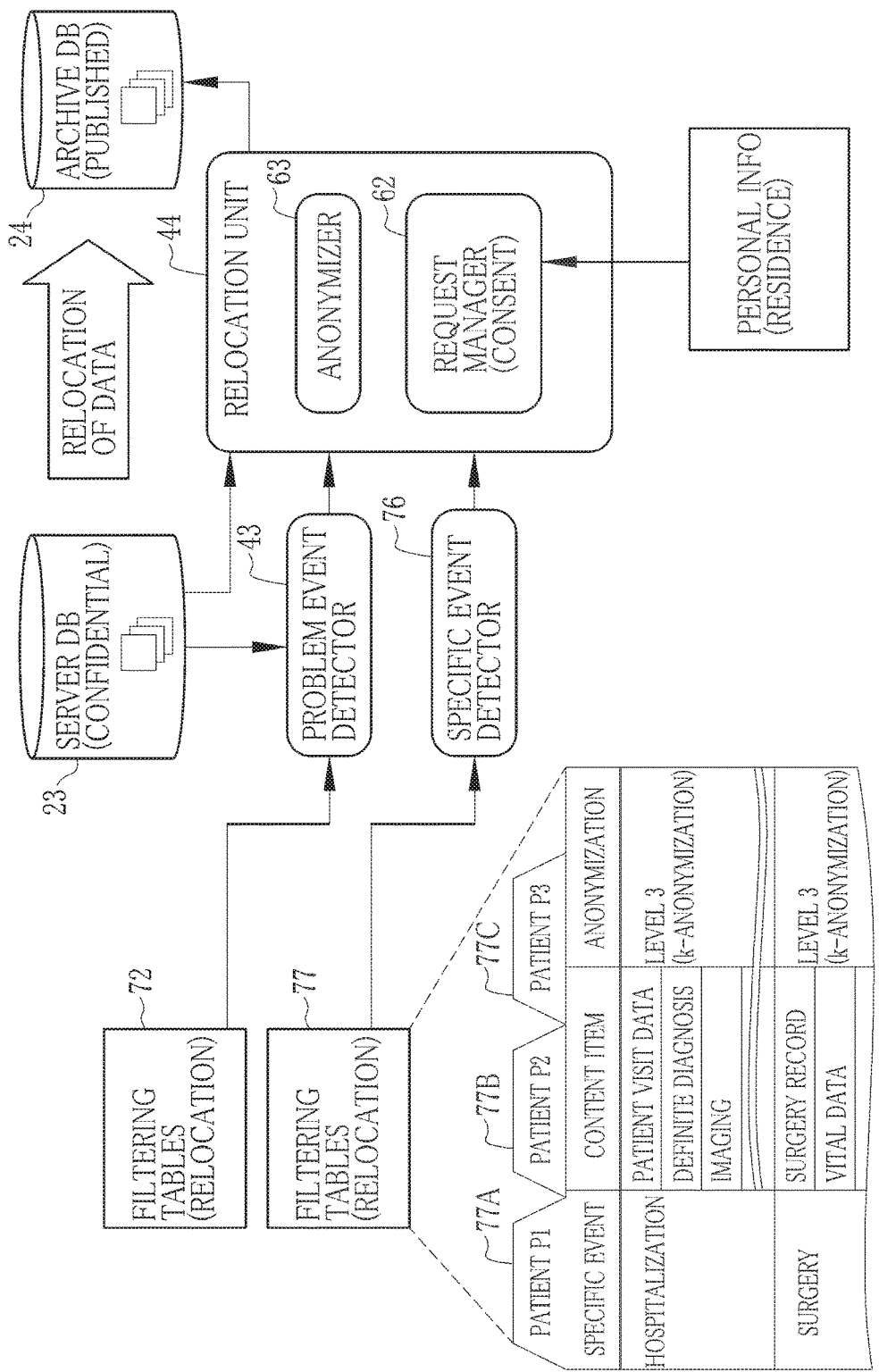
FIG. 18 is a block diagram schematically illustrating a sixth preferred embodiment.

In FIG. 18, a sixth preferred embodiment is illustrated. Preparatory processing for relocation of part of confidential data to published data can be performed even upon occurrence of a specific event in addition to occurrence to a problem event. To this end, a specific event detector 76 and filtering tables (relocation tables) are additionally provided.

In the embodiment, a term of a specific event is used to stand for an event predetermined among the medical events. Examples of the medical events are a first patient visit, hospitalization, hospital discharge, rehospitalization, conversion between hospital departments, medical intervention, surgery (such as gastrectomy), drug administration, complete cure and other events in the course of providing medical care to the respective patients. Also, a problem event is included in the medical events.

The filtering tables 77 contain information of specific events and information of content items of medical care data upon occurrence of the specific events. The specific events are events of a preferred time points for relocation of part of confidential data to published data among medical events other than problem events. While occurrence of a problem event is set in the filtering tables 72, the specific event other than the occurrence of the problem event is set in the filtering tables 77.

Examples of specific events in the filtering tables 77 are hospitalization, surgery and the like. Examples of content items for the hospitalization include patient visit data, definite diagnosis, imaging and the like. Examples of content items of the surgery include surgery record, vital data and the like. Anonymization levels can be determined for each of the specific events, or each of content items. Filtering tables 77A, 77B and 77C (relocation tables) are included in the filtering tables 77 and associated with respectively patients, in the same manner as the filtering tables 72. Information content in the filtering tables 77A-77C can be determined for each of the patients.

The specific event detector 76 monitors addition or updating of confidential data (medical care data) in the server database 23 in the same manner as the problem event detector 43. The specific event detector 76 checks whether a specific event has occurred to each of the patient by referring to the added or updated medical care data and the filtering tables 77. Upon the occurrence of the specific event, the relocation unit 44 starts the preparatory processing for relocating part of the confidential data to the published data.

In the same manner as occurrence of a problem event, medical care data after occurrence of the specific event is relocated to published data after requesting and receiving patient consent of the patient, as indicated in the steps S130-S150 in FIG. 10.

Thus, number of times of collecting published data can be increased by use of occurrence of a specific event as well as the problem event for a flag signal of relocation to published data. This is effective in developing the accumulation of published data.

In the above embodiments, the management server apparatus 16 in the hospital facilities 11 are the information management apparatus of the invention. However, an information management apparatus of the invention can be a common server apparatus for use between the hospital facilities 11 remotely. For example, the medical support server apparatus 12 of FIG. 1 has a function of the common server apparatus, and is caused to constitute the information management apparatus. The common server apparatus is connected to the hospital facilities 11 communicably with the WAN 13. Thus, installation of the information management apparatus is unnecessary in the hospital facilities 11, so that expense for the installation can be lower for medical facilities in view of the investment.

Although the server database 23 and the archive database 24 are combined with the management server apparatus in the above embodiment, it is possible to combine at least one of the server database 23 and the archive database 24 with a server apparatus discrete from the management server apparatus. For example, the server database 23 can be combined with the HIS 14. Also, a server apparatus can include functions of the EMR database 21 and the image database 22. Furthermore, only the server database 23 can be combined with the management server apparatus 16 in each of the hospital facilities 11. The archive database 24 can be combined with the medical support server apparatus 12.

In the invention, each of the patients is requested to give consent in relation to publishing medical care data of the patient. However, it is impossible to make a request to a patient while he or she is in a deep coma, or after his or her death. For such a condition, it is preferable to make a request of consent to the patient's family, in order to relocate medical care data to published data.

Note that published data of the invention are freely usable to various researchers in the medical field. Access can be performed to the published data by use of the Internet or the like. However, it is preferable to provide a login system in a function of access to the published data, so as to perform maintenance and management of the archive database 24 and prevent cyber attack or other improper access to the published data in the archive database 24. Published data as a term used in the present invention includes sample data, general use data or the like protected by security protection with public notice of an access method to the data.

The present invention is not limited to the above embodiments. Various features of the embodiments and variants of the invention can be combined with each other suitably. Also, the computer-executable program and a storage medium for storing the computer-executable program are included in the scope of the present invention.

In a preferred embodiment mode of the present invention, an information sharing apparatus for medical care data of a patient body includes a data uploader for classifying the medical care data into confidential data for a primary use in medical care of the patient body, and published data published for a secondary use different from the primary use, to store the confidential data and the published data in a storage medium. A problem event detector monitors the confidential data being added or updated, to check occurrence of a problem event of clinical exacerbation of the patient body. An activation processor checks occurrence of a flag signal for activating relocation of the confidential data to the published data upon the occurrence of the problem event. A relocation unit filters the confidential data at least partially to produce published data upon occurrence of the flag signal after the occurrence of the problem event.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An information management apparatus for medical care data of a patient body, comprising:
   a data uploader for classifying said medical care data into confidential data for a primary use in medical care of said patient body, and published data published for a secondary use different from said primary use, to store said confidential data and said published data in a storage medium;
   a problem event detector for monitoring said confidential data being added or updated, to check occurrence of a problem event of clinical exacerbation of said patient body; and
   a relocation unit for, assuming that said problem event has occurred, performing preparatory processing in order to relocate said confidential data at least partially to said published data,
   wherein said preparatory processing is transmission of request message information to said patient body for requesting patient consent to publishing said confidential data at least partially,
   wherein said relocation unit performs relocation of said confidential data at least partially to said published data upon receiving said patient consent from said patient body after said request message information,
   wherein assuming that said patient consent is not received even upon lapse of a predetermined time after transmitting said request message information, it is judged in said preparatory processing that presumed patient consent is received, so that said relocation is performed,
   wherein said relocation of said confidential data to said published data after said occurrence of said problem event enhances database of medical research by publishing relevant information of said patient body having said problem event.

2. An information management apparatus as defined in claim 1, further comprising a data output unit for outputting said published data stored in said storage medium.

3. An information management apparatus as defined in claim 1, wherein said problem event is constituted by at least one of occurrence of adverse effect of a drug, occurrence of exacerbation in a diagnostic test value, and medical diagnosis of detecting progress of a disease period of said patient body.

4. An information management apparatus as defined in claim 3, wherein said problem event is occurrence of adverse effect with said drug;
   further comprising:
   a data searcher for searching and detecting a typically grouped patient body to whom said drug has been commonly administered among patient bodies different from patient bodies of detection of said occurrence of said adverse effect;
   a statistical processor for producing statistical data from said confidential data of said typically grouped patient body after detection, said statistical data being in a form with which said patient body is unidentifiable;
   said relocation unit starts said preparatory processing of said confidential data of said patient bodies of said detection of said occurrence of said adverse effect, and relocates said statistic data to said published data.

5. An information management apparatus as defined in claim 1, further comprising a status updater for setting a content item included in said confidential data for relocation to said published data for each type of said problem event.

6. An information management apparatus as defined in claim 5, wherein said content item is settable respectively for said patient body.

7. An information management apparatus as defined in claim 1, wherein said problem event detector further checks occurrence of a specific event predetermined clinically in said medical care of said patient body;
   said relocation unit performs said preparatory processing in case it is judged that said specific event has occurred.

8. An information management apparatus as defined in claim 1, further comprising an anonymizer for anonymizing said confidential data to be relocated to said published data.

9. An information management apparatus as defined in claim 8, wherein said anonymizer performs anonymization of which a level is changeable according to at least one of a type of said problem event and a type of said confidential data to be relocated.

10. An information management apparatus as defined in claim 1, wherein said storage medium includes:
    a first storage area for storing said confidential data; and
    a second storage area, separate from said first storage area physically, for storing said published data.

11. An information management method for medical care data of a patient body, comprising steps of:
    classifying said medical care data into confidential data for a primary use in medical care of said patient body, and published data published for a secondary use different from said primary use, to store said confidential data and said published data in a storage medium;
    monitoring said confidential data being added or updated, to check occurrence of a problem event of clinical exacerbation of said patient body;
    assuming that said problem event has occurred, performing preparatory processing in order to relocate said confidential data at least partially to said published data, wherein said preparatory processing is transmission of request message information to said patient body for requesting patient consent to publishing said confidential data at least partially;

performing relocation of said confidential data at least partially to said published data upon receiving said patient consent from said patient body after said request message information; and assuming that said patient consent is not received even upon lapse of a predetermined time after transmitting said request message information, judging in said preparatory processing that presumed patient consent is received, so that said relocation is performed, wherein said relocation of said confidential data to said published data after said occurrence of said problem event enhances database of medical research by publishing relevant information of said patient body having said problem event.

12. A non-transitory computer readable medium for storing a computer-executable program enabling execution of computer instructions to perform operations for information management for medical care data of a patient body, said operations comprising:

classifying said medical care data into confidential data for a primary use in medical care of said patient body, and published data published for a secondary use different from said primary use, to store said confidential data and said published data in a storage medium;

monitoring said confidential data being added or updated, to check occurrence of a problem event of clinical exacerbation of said patient body;

assuming that said problem event has occurred, performing preparatory processing in order to relocate said confidential data at least partially to said published data, wherein said preparatory processing is transmission of request message information to said patient body for requesting patient consent to publishing said confidential data at least partially;

performing relocation of said confidential data at least partially to said published data upon receiving said patient consent from said patient body after said request message information; and assuming that said patient consent is not received even upon lapse of a predetermined time after transmitting said request message information, judging in said preparatory processing that presumed patient consent is received, so that said relocation is performed, wherein said relocation of said confidential data to said published data after said occurrence of said problem event enhances database of medical research by publishing relevant information of said patient body having said problem event.

* * * * *